US010703775B2

(12) United States Patent
Kimmelshue et al.

(10) Patent No.: US 10,703,775 B2
(45) Date of Patent: Jul. 7, 2020

(54) METHOD OF PURIFYING ANTIFUNGAL COMPOUNDS AND EXOPOLYSACCHARIDES FROM A MICROBIAL CELL CULTURE

(71) Applicant: Bayer CropScience LP, Research Triangle Park, NC (US)

(72) Inventors: Chad Kimmelshue, Ames, IA (US); Yan Li, Citrus Heights, CA (US); Colleen S. Taylor, Folsom, CA (US); Hong Zhu, West Sacramento, CA (US)

(73) Assignee: Bayer CropScience LP, St. Louis, MO (US)

( * ) Notice: Subject to any disclaimer, the term of this patent is extended or adjusted under 35 U.S.C. 154(b) by 93 days.

(21) Appl. No.: 16/080,453

(22) PCT Filed: Mar. 1, 2017

(86) PCT No.: PCT/US2017/020157
§ 371 (c)(1),
(2) Date: Aug. 28, 2018

(87) PCT Pub. No.: WO2017/151742
PCT Pub. Date: Sep. 8, 2017

(65) Prior Publication Data
US 2019/0062370 A1    Feb. 28, 2019

Related U.S. Application Data

(60) Provisional application No. 62/303,171, filed on Mar. 3, 2016.

(51) Int. Cl.
| | |
|---|---|
| *C07K 1/36* | (2006.01) |
| *C07K 1/30* | (2006.01) |
| *C12P 21/02* | (2006.01) |
| *C07K 7/00* | (2006.01) |
| *C12P 19/04* | (2006.01) |
| *C07K 7/64* | (2006.01) |

(52) U.S. Cl.
CPC .......... *C07K 1/36* (2013.01); *C07K 1/30* (2013.01); *C07K 7/00* (2013.01); *C07K 7/64* (2013.01); *C12P 19/04* (2013.01); *C12P 21/02* (2013.01)

(58) Field of Classification Search
CPC ... C07K 1/30; C07K 1/36; C07K 7/00; C07K 7/64; C12P 21/02; H02J 3/14; Y02B 70/3225; Y04S 20/222
See application file for complete search history.

(56) References Cited

U.S. PATENT DOCUMENTS

| | | | | |
|---|---|---|---|---|
| 4,235,966 | A * | 11/1980 | Jarman | C12P 19/04 435/101 |
| 6,066,479 | A * | 5/2000 | Wright | C12P 19/04 435/101 |
| 2009/0136537 | A1 | 5/2009 | Evans et al. | |
| 2013/0331311 | A1* | 12/2013 | Guilhabert-Goya | C07K 7/56 514/3.3 |

FOREIGN PATENT DOCUMENTS

| | | |
|---|---|---|
| EP | 1176209 A1 | 1/2002 |
| WO | 2009/044279 A2 | 4/2009 |

OTHER PUBLICATIONS

Donot, F., et al., "Microbial Exopolysaccharides: Main Examples of Synthesis, Excretion, Genetics and Extraction," Carbohydrate Polymers, Aug. 24, 2011, vol. 87, No. 2, pp. 951-962.
Li, Y., et al., "Polymer/Surfactant Interactions. The Controlled Desorption of Sodium Dodecyl Sulfate (SDS) from a Polymer/SDS Complex in Aqueous Solution," Langmuir, 1996, vol. 12, pp. 4476-4478.
Li, Y., et al., "Moderation of the Interactions between Sodium Dodecyl Sulfate and Poly(vinylpyrrolidone) Using the Nonionic Surfactant Hexaethyleneglycol Mono-n-dodecyl Ether C12EO6: an Electromotive Force, Microcalorimetry, and Small-Angle Neutron Scatting Study," Langmuir, 2000, vol. 16, pp. 8677-8684.
International Search Report and Written Opinion of the International Searching Authority, PCT International Patent Application No. PCT/US2017/020157, dated Apr. 26, 2017, 11 pages.
Madhuri, K.V., et al., "Microbial Exopolysaccharides: Biosynthesis and Potential Applications," Oriental Journal of Chemistry, 2014, vol. 30, No. 3, pp. 1401-1410.
Schmid, J., et al., "Bacterial Exopolysaccharides: Biosynthesis Pathways and Engineering Strategies," Frontiers in Microbiology, May 2015, vol. 6, Article 496, pp. 1-24.

* cited by examiner

Primary Examiner — Susan M Hanley

(57) ABSTRACT

The present invention provides a method of enriching a lipopeptide in a microbial cell culture, the method comprising mixing an amphiphilic sulfonate and/or an amphiphilic sulfate with the cell culture to induce the formation of aggregates containing the lipopeptide, centrifuging the cell culture to generate a supernatant fraction and a pellet fraction, separating the pellet fraction from the supernatant fraction, and mixing the pellet fraction with a polyoxyethylene glycol alkyl ether to release the lipopeptide from the aggregates. Also provided is a method of purifying an exopolysaccharide from a microbial cell culture, the method comprising mixing an amphiphilic sulfonate and/or an amphiphilic sulfate with the cell culture to induce the formation of aggregates, centrifuging the cell culture to generate a supernatant fraction and a pellet fraction, separating the supernatant fraction from the pellet fraction, adding alcohol to the supernatant fraction to precipitate the exopolysaccharide; and removing the precipitated exopolysaccharide from the supernatant fraction.

13 Claims, 18 Drawing Sheets

WB + SDOS    WB - SDOS

WB - SDOS

WB + SDOS

Top: front view; Bottom: rear view

Volume Statistics (Arithmetic)
Calculations from 0.040 μm to 2000 μm

| Mean | S.D. | Variance | d10 | d50 | d90 |
|------|------|----------|-----|-----|-----|
| μm | μm | μm² | μm | μm | μm |
| 55.9 | 85.4 | 7.302 | 0.709 | 5.02 | 210 |
| 7.22 | 13.6 | 186 | 0.578 | 2.12 | 18.6 |

Volume Statistics (Arithmetic)

Calculations from 0.040 µm to 2000 µm

| Mean | S.D. | Variance | d10 | d50 | d90 |
|---|---|---|---|---|---|
| µm | µm | µm² | µm | µm | µm |
| 14.3 | 26.7 | 713 | 0.572 | 2.53 | 53.7 |
| 11.6 | 21.7 | 472 | 0.572 | 2.33 | 41.0 |

Volume Statistics (Arithmetic)

Calculations from 0.040 μm to 2000 μm

| Mean | S.D. | Variance | d10 | d50 | d90 |
|---|---|---|---|---|---|
| μm | μm | μm² | μm | μm | μm |
| 57.3 | 85.5 | 7310 | 1.09 | 13.8 | 177 |
| 33.7 | 51.5 | 2655 | 1.02 | 11.8 | 106 |

Volume Statistics (Arithmetic)
Calculations from 0.040 μm to 2000 μm

| Mean | S.D. | Variance | d10 | d50 | d90 |
|---|---|---|---|---|---|
| μm | μm | μm² | μm | μm | μm |
| 1.03 | 0.656 | 0.430 | 1.333 | 0.866 | 2.00 |
| 1.02 | 0.673 | 0.454 | 0.137 | 0.791 | 2.05 |

Volume Statistics (Arithmetic)

Calculations from 0.040 µm to 2000 µm

| Mean | S.D. | Variance | d10 | d50 | d90 |
|---|---|---|---|---|---|
| µm | µm | µm² | µm | µm | µm |
| 0.263 | 0.366 | 0.134 | 0.074 | 0.092 | 0.997 |
| 0.234 | 0.323 | 0.104 | 0.068 | 0.064 | 0.888 | pH 3      pH 6      pH 10

Front View

Clearest supernatant

Back View

FIG. 9

Effect of Releasing Agent on Fusaricidin A Levels in Pellets Formed with GEROPON® (SDOS)

Front View

NRRL B-21661 WB — GEROPON®    NRRL B-21661 WB + GEROPON®

Back View

← Clearer Supernatant

← More Compact Pellet

METHOD OF PURIFYING ANTIFUNGAL COMPOUNDS AND EXOPOLYSACCHARIDES FROM A MICROBIAL CELL CULTURE

CROSS-REFERENCE TO RELATED APPLICATION(S)

The present application is a 35 U.S.C. § 371 national phase entry of International Application No. PCT/US2017/020157, filed Mar. 1, 2017, which claims the benefit under 35 U.S.C. § 119 of U.S. Provisional Patent Application No. 62/303,171, filed Mar. 3, 2016, the entire contents of which are hereby incorporated herein by reference.

FIELD OF INVENTION

The present invention relates to methods of processing microbial cell cultures to concentrate or purify lipopeptides and exopolysaccharides produced by the microbial cells.

BACKGROUND OF INVENTION

Fungicides have myriad uses, including for crop protection; as food, feed, and cosmetics preservatives; and as therapeutic agents for both human and veterinary applications. Crop yield reduction, foodborne diseases and fungal infections of both humans and animals are a problem in both developed and developing countries.

Synthetic insecticides or fungicides often are non-specific and therefore can act on organisms other than the target organisms, including other naturally occurring beneficial organisms. Because of their chemical nature, they may also be toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i.e., synthetic) pesticides. Thus, there is a need to manage food chain requirements while still allowing effective pest control.

A further problem arising with the use of synthetic insecticides or fungicides is that the repeated and exclusive application of an insecticide or fungicide often leads to selection of resistant pathogenic microorganisms. Normally, such strains are also cross-resistant against other active ingredients having the same mode of action. This eliminates effective control of the pathogens with the active compounds. However, active ingredients having new mechanisms of action are difficult and expensive to develop.

The risk of resistance development in pathogen populations as well as environmental and human health concerns have fostered interest in identifying alternatives to synthetic insecticides and fungicides for managing plant diseases. The use of biological control agents is one alternative.

Non-ribosomal peptides, such as the fusaricidins, are well-recognized for their antimicrobial properties and have been used in the field of crop protection. Because of their mode of action, they also have potential uses in biopharmaceutical and other biotechnology applications. Fusaricidins can be isolated from *Paenibacillus* sp. and have a ring structure composed of 6 amino acid residues in addition to 15-guanidino-3-hydroxypentadecanoic acid. Fusaricidins isolated from *Paenibacillus polymyxa* include LI-F03, LI-F04, LI-F05, LI-F07 and LI-F08 (Kurusu K, Ohba K, Arai T and Fukushima K., J. Antibiotics, 40:1506-1514, 1987) and additional fusaricidins A, B, C and D have been reported (Kajimura Y and Kaneda M., J. Antibiotics, 49:129-135, 1996; Kajimura Y and Kaneda M., J. Antibiotics, 50:220-228, 1997).

Certain fusaricidins are known to have germicidal activity against plant pathogenic fungi such as *Fusarium oxysporum*, *Aspergillus niger*, *Aspergillus oryzae* and *Penicillium thomii*. Some fusaricidins also have germicidal activity against Gram-positive bacteria including *Staphylococcus aureus* (Kajimura Y and Kaneda M., J. Antibiotics, 49:129-135, 1996; Kajimura Y and Kaneda M., J. Antibiotics, 50:220-228, 1997). In addition, it has been found that specific fusaricidins have antifungal activity against *Leptosphaeria maculans* which causes black root rot of canola (Beatty P H and Jensen S E., Can. J. Microbiol., 48:159-169, 2002).

There is a need to identify efficient methods of enriching active compounds such as fusaricidins in fermentation broths. This can be particularly difficult as such fermentation broths often contain high levels of exopolysaccharides (EPS) and other biopolymers that increase the viscosity of the broth and thereby make the enrichment process more challenging.

EPS are high-molecular-weight polymers that are composed of sugar residues and are secreted by many microorganisms into the surrounding environment. Microorganisms synthesize a wide spectrum of multifunctional polysaccharides including intracellular polysaccharides, capsular polysaccharides, and extracellular polysaccharides (EPS). Exopolysaccharides generally consist of modified monosaccharides and, tentatively, some non-carbohydrate substituents such as acetate, pyruvate, succinate, and phosphate.

Many EPS, such as glucans and fructans, are produced extracellularly by the activity of glycosyl- or fructosyl-transferases, respectively, which use the disaccharide sucrose as the main substrate and are secreted by microorganisms into the culture medium. These enzymes cleave sucrose in a first step, and afterwards transfer either glucose or fructose to a growing sugar polymer forming glucans or fructans. The remaining free sugar monomers are subsequently metabolized.

For commercial purposes, EPS are currently isolated from fermentation broths after separation of biomass by downstream processes such as alcoholic precipitation (Donot, F., Fontana, A., Baccou, J. C., & Schorr-Galindo, S., Carbohydrate Polymers, 87:951-962, 2012). Current downstream processing to separate EPS from active compounds in fermentation broths may be costly and degrade the active compounds. The synthesis of viscous biopolymers hinders the fermentation process (i.e., stirring and oxygenation) as well as the recovery of highly purified molecules. There is a need for a cost-effective, efficient method of separating viscous biopolymers from active compounds in fermentation broth while preserving the activity of these compounds.

SUMMARY OF THE INVENTION

The present invention is directed to a method of enriching a lipopeptide in a microbial cell culture, the method comprising: a) mixing an amphiphilic sulfonate and/or an amphiphilic sulfate with the cell culture to induce the formation of aggregates containing the lipopeptide; b) centrifuging the cell culture to generate a supernatant fraction and a pellet fraction; c) separating the pellet fraction from the supernatant fraction; and d) mixing the pellet fraction with a polyoxyethylene glycol alkyl ether to release the lipopeptide from the aggregates.

In certain aspects, the lipopeptide is selected from the group consisting of iturin-type compounds, fengycin-type compounds, surfactin-type compounds, fusaricidin-type compounds, and combinations thereof. In one aspect, the lipopeptide is a fusaricidin-type compound.

In some embodiments, the fusaricidin-type compound is selected from the group consisting of fusaricidin A, fusaricidin B, fusaricidin C, fusaricidin D, LI-F03, LI-F04, LI-F05, LI-F06, LI-F07, LI-F08, Paeniserine A1, Paeniserine A2, Paeniserine A3, Paeniserine A4, Paeniserine B1., Paeniserine B2, Paeniserine B3, Paeniserine B4, Paeniserine C1, Paeniserine C2, Paeniserine C3, Paeniserine C4, Paeniprolixin A1, Paeniprolixin A2, Paeniprolixin B1, Paeniprolixin B2, Paeniprolixin C1, Paeniprolixin C2, Paeniprolixin D1, Paeniprolixin D2, Paeniprolixin E1, Paeniprolixin E2, Paeniprolixin F1, Paeniprolixin F2, and combinations thereof.

In other embodiments, an amphiphilic sulfonate is mixed with the cell culture and the amphiphilic sulfonate is a compound of formula (I):

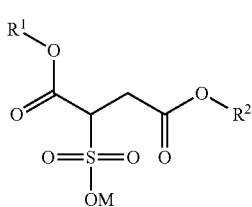

(I)

wherein $R^1$ and $R^2$ are independently a linear or branched $C_{1-20}$ alkyl or a linear or branched $C_{2-20}$ alkene; and M is $H^+$, $Li^+$, $Na^+$, $K^+$ or $(C_{1-8}\ alkyl)_4N^+$. In one aspect, $R_1$ and $R_2$ are independently linear or branched $C_8$ alkyl. In another aspect, the sulfonate is dioctyl sulfosuccinate; 1,4-bis(2-ethylhexoxy)-1,4-dioxobutane-2-sulfonate; or a $Li^+$, $Na^+$, $K^+$ or $(C_{1-8}\ alkyl)_4N^+$ salt thereof.

In other embodiments, an amphiphilic sulfate is mixed with the cell culture and the amphiphilic sulfate is an alkyl sulfate. In one embodiment, the alkyl sulfate is a compound of formula (II):

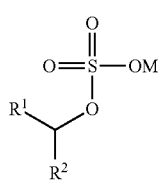

(II)

wherein $R^1$ and $R^2$ are independently H, a linear or branched $C_{1-20}$ alkyl, or a linear or branched $C_{2-20}$ alkene; and M is $H^+$, $Li^+$, $Na^+$, $K^+$ or $(C_{1-8}\ alkyl)_4N^+$; with the proviso that $R^1$ and $R^2$ are not both H. In one aspect, $R^1$ and $R^2$ are independently a branched $C_{3-20}$ alkyl. In another aspect, the alkyl sulfate is 7-ethyl-2-methyl-4-undecanyl sulfate or a $Li^+$, $Na^+$, $K^+$ or $(C_{1-8}\ alkyl)_4N^+$ salt thereof. In yet another aspect, $R^1$ is H and $R^2$ is a branched $C_{3-20}$ alkyl. In one embodiment, the alkyl sulfate is 2-ethylhexyl sulfate or a $Li^+$, $Na^+$, $K^+$ or $(C_{1-8}\ alkyl)_4N^+$ salt thereof.

In other embodiments, an amphiphilic sulfonate is mixed with the cell culture and the amphiphilic sulfonate is a linear alkylbenzenesulfonate or a branched alkylbenzenesulfonate. In certain embodiments, the amphiphilic sulfonate is a linear alkylbenzenesulfonate of formula (III):

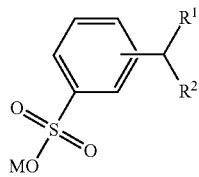

(III)

wherein $R^1$ and $R^2$ are independently H or a linear $C_{1-20}$ alkyl; and M is $H^+$, $Li^+$, $Na^+$, $K^+$ or $(C_{1-8}\ alkyl)_4N^+$; with the proviso that $R^1$ and $R^2$ are not both H. In one embodiment, $R^1$ and $R^2$ form a $C_{10-16}$ alkyl chain. In another embodiment, the linear alkylbenzenesulfonate is dodecylbenzesulfonate or a $Li^+$, $Na^+$, $K^+$ or $(C_{1-8}\ alkyl)_4N^+$ salt thereof.

In certain aspects, the polyoxyethylene glycol alkyl ether is a compound with a molecular formula of $C_nH_{2n-1}(OCH_2CH_2)_mOH$, wherein m is an integer between 1 and 120; and n is an integer between 1 and 20. In some aspects, n is 8, 10, 12, 14, 16, 18, or 20. In one aspect, n is 12 or 18. In yet other aspects, m is an integer between 5 and 100. In one embodiment, m is 25. In another embodiment, m is 100.

In yet other embodiments, the present invention is directed to a method of purifying an exopolysaccharide (EPS) from a microbial cell culture, the method comprising: a) mixing an amphiphilic sulfonate and/or an amphiphilic sulfate with the cell culture to induce the formation of aggregates, b) centrifuging the cell culture to generate a supernatant fraction and a pellet fraction; c) separating the supernatant fraction from the pellet fraction; d) adding alcohol to the supernatant fraction to precipitate the EPS; and e) removing the precipitated EPS from the supernatant fraction.

In certain aspects, EPS is selected from glucan, fructan, curdlan, gellan, xanthan, emulsan, dextran, cellulose, and combinations thereof.

In still other embodiments, the present invention is directed to a method of purifying an a water-soluble, biopolymer from a microbial cell culture, the method comprising: a) mixing an amphiphilic sulfonate and/or an amphiphilic sulfate with the cell culture to induce the formation of aggregates; b) centrifuging the cell culture to generate a supernatant fraction and a pellet fraction; c) separating the supernatant fraction from the pellet fraction; d) adding alcohol to the supernatant fraction to precipitate the biopolymer; and e) removing the precipitated biopolymer from the supernatant fraction.

In yet other aspects, the pH of the microbial cell culture is adjusted to between about 4 and about 7 prior to mixing with the amphiphilic sulfonate and/or the amphiphilic sulfate. In one aspect, the pH of the microbial cell culture is adjusted to about 6.

In still other embodiments, a salt is added to the microbial cell culture at a concentration of about 0.5% to about 5% prior to centrifuging. In one embodiment, sodium chloride or potassium chloride is added to the microbial cell culture at a concentration of about 2%.

In another aspect, the microbial cell culture comprises a strain of *Paenibacillus* sp., *Bacillus* sp., and/or *Pseudomonas* sp. In one embodiment, the microbial cell culture comprises *Paenibacillus* sp. strain NRRL B-50972, *Bacillus subtilis* strain NRRL B-21661, and/or a fungicidal mutant strain thereof having all the identifying characteristics of the respective strain.

FIG. 2 depicts photographs of pellets from *Paenibacillus* sp. NRRL B-50972 whole broth centrifuged without any centrifuge aid labeled "WB−SDOS" and centrifuged whole broth mixed with GEROPON® (SDOS) labeled "WB+SDOS".

FIG. 3 depicts pellets formed after centrifugation for 5 minutes at an RCF of 17,000×g with or without GEROPON® (SDOS) of a whole broth from another *Paenibacillus* strain known to produce relatively high levels of EPS.

FIG. 4 depicts relative quantification of fusaricidin A in pellet and supernatant fractions containing GEROPON® (SDOS) or purified SDOS.

FIGS. 5A-5E depict a particle size analysis of broth concentrates and supernatants produced from *Paenibacillus* sp. NRRL B-50972 whole broth centrifuged with or without GEROPON® (SDOS).

FIG. 6 depicts photographs of pellets formed from *Paenibacillus* sp. NRRL B-50972 whole broth adjusted to a pH of 3, 6, or 10 and centrifuged with GEROPON® (SDOS).

FIG. 7A depicts photographs of pellets formed when *Paenibacillus* sp. NRRL B-50972 whole broth with other chemical compounds besides GEROPON® (SDOS). FIG. 7B depicts a photograph of the pellet and supernatant fractions a larger scale experiment confirming that NIAPROOF® 4 (sodium 7-ethyl-2-methyl-4-undecanyl sulfate) produces a similar effect to GEROPON® (SDOS).

FIG. 8 depicts relative quantification of fusaricidin A in a supernatant fraction and pellet fractions containing GEROPON® (SDOS) alone or in combination with polyoxyethylene (25) dodecyl ether (also known as C12EO25) or BRIJ® L23 (polyoxyethylene (23) dodecyl ether; also known as C12EO23).

FIG. 9 depicts relative quantification of fusaricidin A in pellet fractions containing GEROPON® (SDOS) alone or in combination with one of several chemical compounds that act as releasing aids.

FIG. 10 depicts the increased suspensibility of a pellet fraction after addition of the releasing aid, C12E025.

FIG. 11 depicts relative quantification of fusaricidin A in five batches of *Paenibacillus* sp. NRRL B-50972 whole broth and the corresponding broth concentrates using GEROPON® (SDOS) as a centrifuge aid and BRIJ® S100 (polyoxyethylene (100) octadecyl ether) as a releasing aid.

FIG. 12 depicts pellets formed after centrifugation for 5 minutes at an RCF of 1,500×g with or without GEROPON® (SDOS) of a viscous whole broth (WB) from *Bacillus subtilis* strain NRRL B-21661.

FIG. 13 depicts relative quantification of fusaricidin A in whole broths ("WB") and the corresponding supernatants ("Sup") and broth concentrates ("BC") produced with GEROPON® (SDOS) as a centrifuge aid and BRIJ® S100 (polyoxyethylene (100) octadecyl ether) as a releasing aid with *Paenibacillus* sp. NRRL B-50972 and two other *Paenibacillus* strains.

DETAILED DESCRIPTION OF THE INVENTION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "amphiphilic" describes a chemical compound possessing both hydrophilic and lipophilic properties.

In certain aspects, the amphiphilic sulfonate and/or an amphiphilic sulfate are mixed with the cell culture at a concentration (% w/v) of about 0.01% to about 1.0%; e.g., any range within about 0.01% to about 1.0% such as about 0.01% to about 0.5%, about 0.05% to about 0.2%, about 0.1% to about 0.2%, etc.

In other aspects, the amphiphilic sulfonate and/or an amphiphilic sulfate are mixed with the cell culture at a concentration (% w/v) of at least 0.01%, at least 0.02%, at least 0.03%, at least 0.04%, at least 0.05%, at least 0.06%, at least 0.07%, at least 0.08%, at least 0.090%, at least 0.10%, at least 0.12%, at least 0.14%, at least 0.16%, at least 0.18%, or at least 0.20%.

In certain aspects, the polyoxyethylene glycol alkyl ether is mixed with the pellet fraction or the supernatant fraction at a concentration (% w/v) of about 0.01% to about 1.0%; e.g., any range within about 0.01% to about 1.0% such as about 0.01% to about 0.5%, about 0.05% to about 0.2%, about 0.1% to about 0.2%, etc.

In other aspects, the polyoxyethylene glycol alkyl ether is mixed with the pellet fraction or the supernatant fraction at a concentration (% w/v) of at least 0.01%, at least 0.02%, at least 0.03%, at least 0.04%, at least 0.05%, at least 0.06%, at least 0.07%, at least 0.08%, at least 0.09%, at least 0.10%, at least 0.12%, at least 0.14%, at least 0.16%, at least 0.18%, or at least 0.20%.

In yet other aspects, the ratio (w/w) of amphiphilic sulfonate and/or an amphiphilic sulfate to polyoxyethylene glycol alkyl ether mixed with the cell culture or fractions derived therefrom is about 50:1 to about 1:50; e.g., any range within about 50:1 to about 1:50 such as about 40:1 to about 1:40, about 30:1 to about 1:30, about 25:1 to about 1:25, about 20:1 to about 1:20, about 15:1 to about 1:15, about 10:1 to about 1:10, about 5:1 to about 1:5, or about 2:1 to about 1:2.

In some aspects, the ratio (w/w) of amphiphilic sulfonate and/or an amphiphilic sulfate to polyoxyethylene glycol alkyl ether mixed with the cell culture or fractions derived therefrom is about 10:1, about 9:1, about 8:1, about 7:1, about 6:1, about 5:1, about 4:1, about 3:1, about 1:1, about 1:2, about 1:3, about 1:4, about 1:5, about 1:6, about 1:7, about 1:8, about 1:9, or about 1:10.

In some embodiments, the cell culture is centrifuged at a speed of at least 5,000 RCF, at least 10,000 RCF, at least 15,000 RCF, at least 20,000 RCF, at least 25,000 RCF, at least 30,000 RCF, at least 35,000 RCF, or at least 40,000 RCF.

In certain aspects, the pellet fraction is mixed with a polyoxyethylene derivative of a sorbitan ester of a carboxylic acid to release the lipopeptides from the aggregates. In one embodiment, the polyoxyethylene derivative of a sorbitan ester of a carboxylic acid is a compound of formula (IV):

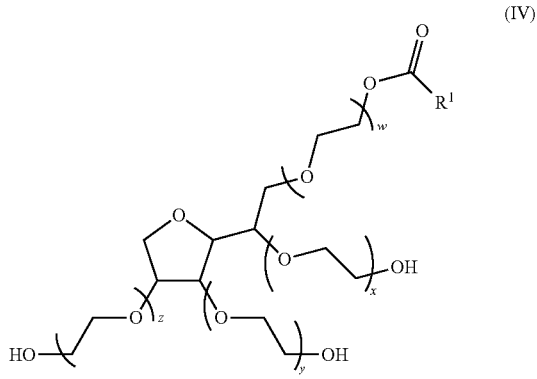

(IV)

Figure 1:
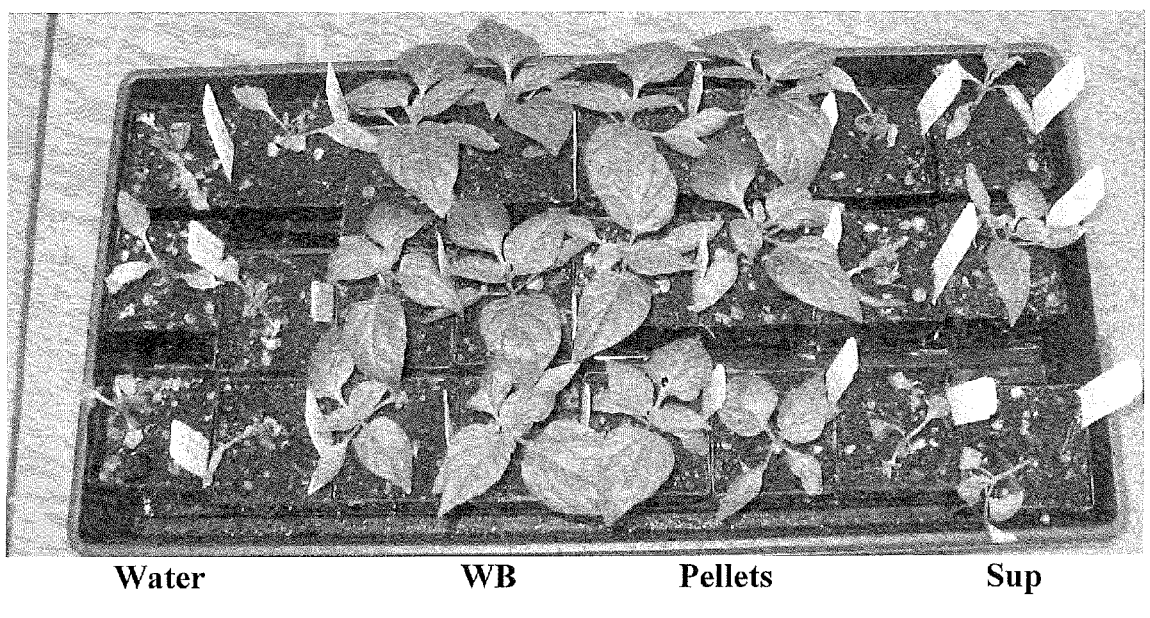
FIG. 1 depicts antifungal activities measured with young plants inoculated with *Botrytis cinerea* (BOTRCI). The antifungal activities of *Paenibacillus* sp. NRRL B-50972 whole broth ("WB") and a pellet fraction ("Pellets") and supernatant fraction ("Sup") formed after centrifugation of the whole broth at an RCF of 24,790×g were compared to untreated control ("Water").

wherein $R^1$ is a $C_{6-18}$ alkyl or a $C_{6-18}$ alkenyl and w+x+y+z=20. In one embodiment, the compound of formula (IV) is TWEEN® 80 (2-[2-[3,4-bis(2-hydroxyethoxy)oxolan-2-yl]-2-(2-hydroxyethoxy)ethoxy]ethyl (E)-octadec-9-enoate; also known as polyoxyethylene sorbitan oleate).

Sodium Dioctyl Sulfosuccinate is marketed under several commercial names including GEROPON DOS®, AEROSOL® OT, TERMUL® 3667, TERMUL® 3665, LANKROPOL® KPH70, and SYNERGEN® W10.

Lipopeptides include but are not limited to amphiphilic cyclic peptides obtainable from various bacteria, including *Bacillus* sp., *Paenibacillus* sp., *Pseudomonas* sp., and *Streptomyces* sp.

In one aspect, the microbial cell culture comprises a strain of *Paenibacillus* sp. In another aspect, the microbial cell culture comprises a strain from any one of the following *Paenibacillus* species: *P. agarexedens, P. agaridevorans, P. alginolyticus. P. alkaliterrae, P. alvei, P. amylolyticus, P. anaericanus, P. antarcticus, P. assamensis, P. azoreducens, P. azotofixans, P. barcinonensis, P. borealis, P. brasiliensis, P. brassicae, P. campinasensis. P. chinjuensis, P. chitinolyticus, P. chondroitinus, P. cineris, P. cookie, P. curdlanolyticus, P. daejeonensis, P. dendritiformis, P. durum, P. ehimensis, P. elgii, P. favisporus, P. glucanolyticus, P. glycanilyticus. P. gordonae, P. graminis, P. granivorans, P. hodogayensis, P. illinoisensis, P. jamilae, P. kobensis, P. koleovorans, P. koreensis, P. kribbensis, P. lactis, P. larvae, P. lautus, P. lentimorbus, P. macerans, P. macquariensis, P. massiliensis, P. mendelii. P. motobuensis, P. naphthalenovorats, P. nematophilus, P. odorifer, P. pabuli, P. peoriae, P. phoenicis, P. phyllosphaerae, P. polymyxa, P. popilliae, P. pulvifaciens, P. rhizosphaerae, P. sanguinis, P. stellifer, P. terrae, P. thiaminolyticus, P. timonensis, P. tvlopili, P. turicensis, P. validus, P. vortex, P. vulneris, P. wylmii, P. xylanilyticus*, and combinations thereof.

In another aspect, the microbial cell culture comprises a strain of *Bacillus* sp. In certain aspects, the microbial cell culture comprises a strain from any one of the following *Bacillus* species: *B. acidiceler, B. acidicola, B. acidiproducens, B. aeolius, B. aerius, B. aerophilus, B. agaradhaerens, B. aidingensis, B. akibai, B. alcalophilus, B. algicola, B. alkalinitrilicus, B. alkalisediminis, B. alkalitelluris, B. altitudinis, B. alveayuensis, B. amyloliquefaciens, B. anthracis, B. aquimaris, B. arsenicus, B. aryabhattai, B. asahii, B. atrophaeus, B. aurantiacus, B. azotoformans, B. badius, B. barbaricus, B. bataviensis, B. beijingensis, B. benzoevorans, B. beveridgei, B. bogoriensis, B. boroniphilus, B. butanolivorans, B. canaveralius, B. carboniphilus, B. cecembensis, B. cellulosilyticus, B. cereus, B. chagannorensis, B. chungangensis, B. cibi, B. circulans, B. clarkii, B. clausii, B. coagulans, B. coahuilensis, B. cohnii, B. decisifrondis, B. decolorationis, B. drentensis, B. farraginis, B. fastidiosus, B. firmus, B. flexus, B. foraminis, B. fordii, B. foris, B. fumarioli, B. funiculus, B. galactosidilyticus, B. galliciensis, B. gelatini, B. gibsonii, B. ginsengi, B. ginsengihumi, B. graminis, B. halmapalus, B. halochares, B. halodurans, B. hemicellulosilyticus, B. herbertsteinensis, B. horikoshi, B. horneckiae, B. horti, B. humi, B. Mhwajinpoensis, B. idriensis, B. indicus, B. infantis, B. infernus, B. isabeliae, B. isronensis, B. jeotgali, B. koreensis, B. korlensis, B. kribbensis, B. krulwichiae, B. lehensis, B. lentus, B. licheniformis, B. litoralis, B. locisalis, B. luciferensis, B. luteolus, B. macauensis, B. macyae, B. mannanilyticus, B. marflavi, B. marmarensis, B. massiliensis, B. megaterium, B. methanolicus, B. methylotrophicus, B. mojavensis, B. muralis, B. murimartini, B. mycoides, B. nanhaiensvis, B. nanhaiisediminis, B. nealsonii, B. neizhouensis, B. niabensis, B. niacini, B. novalis, B. oceanisediminis, B. odysseyi, B. okhensis, B. okuhidensis, B. oleronius, B. oshimensis, B. panaciterrae, B. patagoniensis, B. persepolensis, B. plakortidis, B. pocheonensis, B. polygoni, B. pseudoalcaliphilus, B. pseudofirmus, B. pseudomycoides, B. psychrosaccharolyticus, B. pumilus, B. qingdaonensis, B. rigui, B. ruris, B. safensis, B. salarius, B. saliphilus, B. schlegelii, B. selenatarsenatis, B. selenitireducens, B. seohaeanensis, B. shackletonii, B. siamensis, B. simplex, B. siralis, B. smithii, B. soli, B. solisalsi, B. sonorensis, B. sporothermodurans, B. stratosphericus, B. subterraneus, B. subtilis, B. taeansis, B. tequilensis, B. thermantarcticus, B. thermoamvlovorans, B. thermocloacae, B. thermolactis, B. thioparans, B. thuringiensis, B. tripoxylicola, B. tusciae, B. vallismortis, B. vedderi, B. vietnamensis, B. vireti, B. wakoensis, B. weihenstephanensis, B. xiaoxiensis*, and combinations thereof. In another aspect, the microbial cell culture comprises a strain of *Pseudomonas* sp. In certain aspects, the microbial cell culture comprises a strain from any one of the following *Pseudomonas* species: *P. antarctica, P. azotoformans, P. blatchfordae, P. brassicacearum, P. brenneri, P. cedrina P. corrugate, P. fluorescens, P. gessardii. P. libanensis, P. mandelii, P. marginalis, P. mediterranea, P. meridian, P. migulae, P. mucidolens, P. orientalis, P. panacis, P. protegens. P. proteolytica, P. rhodesiae, P. synxantha, P. thivervalensis, P. tolaasii, P. veronii*, and combinations thereof.

As used herein the term "lipopeptides" may refer to amphiphilic cyclic peptides and antimicrobial peptides.

Amphiphilic cyclic peptides are generally composed of several α-amino acids linked to a β-amino or β-hydroxy fatty acid, including but not limited to fengycin-type compounds, iturin-type compounds, surfactin-type compounds, fusaricidins, viscosins, amphisins, tolaasins, syringomycins, and putisolvins. The iturin-type compounds are composed of seven amino acids and are linked to a β-amino fatty acid. The length of the fatty acid chain of certain lipopeptides varies from C14 to C17. These compounds are obtainable from various species of *Bacillus*, including *subtilis* and *amyloliquefaciens*. The iturins and their variants are described in Ongena, et al., "*Bacillus* Lipopeptides: Versatile Weapons for Plant Disease Biocontrol," Trends in Microbiology, 16(3):115-125, (2007).

Iturin-type compounds of the present invention include one or more of the following compounds: bacillomycin D, bacillyomycin F, bacillomycin L, bacillomycin LC (also known as bacillopeptin), mycosubtilin, iturin A, iturin AL, and iturin C (with the latter three compounds referred to herein, collectively, as iturins).

Fengycin-type compounds are composed of ten amino acids linked to a β-hydroxy fatty acid with a chain that varies in length from C14 to C18. These compounds are obtainable from various species of *Bacillus*, including *subtilis, amyloliquefaciens, cereus* and *thuringiensis* and from *Streptomyces* sp. The fengycin-type compounds are described in Ongena, supra. Fengycin-type compounds suitable for the compositions described herein include fengycin A, fengycin B, plipastatin A, plipastatin B, the plipastatins from a *Streptomyces* sp. described in Kimura, et al., "SNA 60-367—New Peptide Enzyme Inhibitors Against Aromatase," Journal of Antibiotics, 50(6): 529-531, (1997), and agrastatins, as described in U.S. Pat. No. 6,291,426 (with the latter four listings referred to herein, collectively, as plipastatins).

Surfactin-type compounds are composed of seven amino acids linked to a β-hydroxy fatty acid with a chain that varies in length from C13 to C16. These compounds are obtainable from various species of *Bacillus*, including *subtilis, amyloliquefaciens, coagulans, pumilus* and *licheniformis*. The surfactin family of compounds is described in Ongena, supra. Surfactin-type compounds of the present invention include one or more of the following compounds: esperin, lichenysin, pumilacidin and surfactin.

Fusaricidin-type compounds are composed of six amino acids linked to a 15-guanidino-3-hydroxypentadecanoic acid. These compounds are obtainable from *Paenibacillus* sp., including *polymyxa*. The fusaricidin family of compounds is described in Choi, S-K, et al., "Identification and Functional Analysis of the Fusaricidin Biosynthetic Gene of *Paenibacillus polymyxa* E681," Biochemical and Biophysical Research Communications, 365:89-95, (2008). Fusaricidin-type compounds of the present invention include one or more of the following compounds: fusaricidins A, B. C, and D and fusaricidins LI-F03, LI-F04, LI-F05, LI-F06, LI-F07 and LI-F08. Additional fusaricidin-type compounds include the Paeniserines and the Paeniprolixins described in U.S. Patent Application No. 62/232,205, filed on Sep. 24, 2015, which is hereby incorporated by reference. Examples of the Paeniserines and the Paeniprolixins include Paeniserine A1, Paeniserine A2, Paeniserine A3, Paeniserine A4, Paeniserine B1, Paeniserine B2, Paeniserine B3, Paeniserine B4, Paeniserine C1, Paeniserine C2, Paeniserine C3, Paeniserine C4, Paeniprolixin A1, Paeniprolixin A2, Paeniprolixin B1, Paeniprolixin B2, Paeniprolixin C1, Paeniprolixin C2, Paeniprolixin D1, Paeniprolixin D2, Paeniprolixin E1, Paeniprolixin E2, Paeniprolixin F1, and Paeniprolixin F2.

Viscosins, amphisins, tolaasins, syringomycins, and putisolvins are produced by plant-associated *Pseudomonas* spp. as described in Raaijmakers, et al., (2006) Molecular Plant-Microbe Interactions 19(7): 699-710. Viscosins include viscosin, viscosin-amide, massetolide A, massetolide D, WLIP, pseudophomin A, and pseudophomin B. Amphisins include amphisin, tensin, pholipeptin A, lokisin, and arthrofactin. Tolaasins include tolaasin, FP-B. corpeptin A, SP22, and SP25A. The syringomycins include syringomycin, syringostatin, syringotoxin, pseudomycin A, and cormycin A. The putisolvins include putisolvin I and putisolvin II.

Antimicrobial peptides are described in Wang & Wang (2004) Nucleic Acids Research 32: D590-D592. The antimicrobial peptides may be a non-ribosomally synthesized peptide or ribosomally synthesized peptides (RAMP). Non-ribosomally synthesized peptides are found in bacteria and fungi. These antimicrobial peptides are assembled by peptide synthetases as opposed to ribosomal-supported synthesis. Gramicidin (e.g., Gramicidin S, Gramicidin D), bacitracin, polymyxin B. melittin, cecropin, and vancomycin are examples of non-ribosomally synthesized antimicrobial peptides. Zeitler, et al. (2013) PLOS One 8(8): e71687. Further Pantocin A, pantocin B. polyoxins, nikkomycins, rhizocitin, bacilysin, blasticidin, and mildiomycin are all antimicrobial peptides active against plant pathogens that may be used in the claimed compositions or methods. PEP6, PAF26, BPC194, PEP3, PEP11, BP76, CAMEL, Iseganan, D4E1, TYP, ESF12, ESF1, Pexiganan, MSI-99, MB-39, Pen4-1, and D32R are all synthetic antimicrobial peptides with activity against plant pathogens that may be used in the claimed compositions or methods. Additionally, cecropin A, B. tachyplesin, heliomicin/drosomycin, sacrotoxin IA, mussel defensin, magainin, esculentin-1, Rs-AFP2, Alf-AFP, Spi1, DRR230-a, BSD1, WT1, Dm-AMP1, Mj-AMP1, Pn-AMP, hordonthionin, alpha thionin, AFP, SB-37, Shiva-1, SB37, MB-39, MsrA1, MSI-99, Myp30, Rev4, and D4E1 have all been expressed in transgenic plants that confer at least partial resistance to pathogens and may be used in the compositions and methods described herein. Montesinos (2007) FEMS Microbiol Lett 270: 1-11.

A non-limiting list of the EPS that can be purified with the methods disclosed herein includes acetan (*Acetobacter xylimim*); alginate (*Azotobacter vinelandii*); cellulose (*Acetobacter xylinum*); chitosan (*Mucorales* spp.); curdlan (*Alcaligenes faecalis* var. *myrogenes*); cyclosophorans (*Agrobacterium* spp., *Rhizobium* spp. and *Xanthomonas* spp.); dextran (*Leuconostoc mesenteroides, Leuconostoc dextranicum* and *Lactobacillus hilgardii*); emulsan (*Acinetobacter calcoaceticus*); galactoglucopolysaccharides (*Achromobacter* spp., *Agrobacterium radiobacter, Pseudomonas marginalis, Rhizobium* spp. and *Zooglea* spp.); galactosaminogalactan (*Aspergillus* spp.); gellan (*Aureomonas elodea* and *Sphingomonas paucimobilis*); glucuronan (*Sinorhizobium meliloti*); N-acetylglucosamine (*Staphylococcus epidermidis*); N-acetyl-heparosan (*Escherichia coli*); hyaluronic acid (*Streptococcus equi*); indican (*Beijerinckia indica*); kefiran (*Lactobacillus hilgardii*); lentinan (*Lentinus elodes*); levan (*Alcaligenes viscosus, Zymomonas mobilis, Bacillus subtilis*); pullulan (*Aureobasidium pullulans*); scleroglucan (*Sclerotium rolfsii, Sclerotium delfinii* and *Sclerotium glucanicum*); schizophyllan (*Schizophylum commune*); stewartan (*Pantoea stewartii* subsp. *stewartii*); succinoglycan (*Alcaligenes faecalis* var *myxogenes, Sinorhizobium meliloti*); xanthan (*Xanthomonas campestris*); and welan (*Alcaligenes* spp.).

The disclosed methods may be used with compositions obtained by culturing microbial strains (e.g., *Paenibacillus* sp. strain NRRL B-50972, *Bacillus subtilis* strain NRRL B-21661, or a fungicidal mutant (strain) derived therefrom) according to methods well known in the art. Conventional large-scale microbial culture processes include submerged fermentation, solid state fermentation, or liquid surface culture. Towards the end of fermentation, as nutrients are depleted, cells begin the transition from growth phase to sporulation phase, such that the final product of fermentation is largely spores, metabolites and residual fermentation medium. Sporulation is part of the natural life cycle of *Paenibacillus* and is generally initiated by the cell in response to nutrient limitation. Fermentation is configured to obtain high levels of colony forming units of and to promote sporulation. The bacterial cells, spores and metabolites in culture media resulting from fermentation may be used directly or concentrated by industrial methods, such as centrifugation, tangential-flow filtration, depth filtration, and evaporation.

Such compositions include fermentation products. In some embodiments, the concentrated fermentation broth is washed, for example, via a diafiltration process, to remove residual fermentation broth and metabolites. The term "broth concentrate," as used herein, refers to whole broth (fermentation broth) that has been concentrated by industrial methods, as described herein, but remains in liquid form. The term "fermentation solid," as used herein, refers to the solid material that remains after the fermentation broth is dried. The term "fermentation product," as used herein, refers to whole broth, broth concentrate and/or fermentation solids. The methods of the present invention can be used to make compositions that include fermentation products.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the strains of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

In some embodiments, the disclosed methods are produce compositions that are liquid formulations. Non-limiting examples of liquid formulations include suspension concentrations and oil dispersions. In other embodiments, the inventive compositions are solid formulations. Non-limiting examples of liquid formulations include freeze-dried powders and spray-dried powders.

Compositions made with the methods of the present invention may include formulation inerts added to compositions comprising cells, cell-free preparations or metabolites to improve efficacy, stability, and usability and/or to facilitate processing, packaging and end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments", Annu. Rev. Phytopathol. 28: 321-339 (1990). The stabilization agents may include anti-caking agents, anti-oxidation agents, desiccants, protectants or preservatives. The nutrients may include carbon, nitrogen, and phosphors sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, antifreeze agents or colorants. In some embodiments, the composition comprising cells, cell-free preparation or metabolites produced by fermentation can be used directly with or without water as the diluent without any other formulation preparation. In some embodiments, the formulation inerts are added after concentrating fermentation broth and during and/or after drying.

DEPOSIT INFORMATION

A sample of a *Paenibacillus* sp. strain of the invention has been deposited with the Agricultural Research Service Culture Collection located at the National Center for Agricultural Utilization Research, Agricultural Research Service, U.S. Department of Agriculture (NRRL), 1815 North University Street, Peoria, Ill. 61604, U.S.A., under the Budapest Treaty on Aug. 28, 2014, and has been assigned the following accession number: NRRL B-50972. A sample of the *Bacillus subtilis* strain of the invention has been deposited with the NRRL under the Budapest Treaty on May 7, 1997, and assigned the following accession number: NRRL B-21661.

The *Paenibacillus* sp. strain and *Bacillus subtilis* strain have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited *Paenibacillus* sp. strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The following examples are given for purely illustrative and non-limiting purposes of the present invention.

EXAMPLES

Example 1. Fusaricidin A Levels and Antifungal Activity in the Pellet and Supernatant Fractions from a Whole Broth of *Paenibacillus* sp. NRRL B-50972

*Paenibacillus* sp. NRRL B-50972 was grown in a soy-based medium to produce a whole broth culture. A portion of the whole broth culture was then centrifuged at a relative centrifugal force (RCF) of 24,790×g for 10 minutes to produce a pellet fraction (i.e., broth concentrate) and a supernatant. Centrifugation at this speed was only possible for small volumes (~30 mL) and resulted in a soft pellet fraction and relatively cloudy supernatant. The pellet fraction accounted for between one-fourth and one-third of the original volume, and the supernatant fraction accounted for the remaining volume. The pellet fraction and the supernatant fraction were analyzed in these volumes without any further dilution or concentration.

With larger volumes (~1,000 mL) where the maximum centrifugation speed was limited to an RCF of 17,000×g it was not possible to separate a pellet fraction from a supernatant fraction with the viscous *Paenibacillus* sp. NRRL B-50972 whole broth culture. It was evident that large scale centrifugation of the *Paenibacillus* sp. NRRL B-50972 whole broth culture would require modification of the whole broth culture to allow separation of a pellet fraction and a supernatant fraction at lower centrifugation speeds.

A chromatographic method using ultra performance liquid chromatography/mass spectrometry triple time of flight (UPLC/MS Triple TOF) was used to evaluate the relative quantities of the known antifungal compound, fusaricidin A, in the fractions: Column: ZORBAX™ Eclipse Plus, 2.1×100 mm, 1.8 μm; Water (0.1% FA) and acetonitrile (0.1% FA); Gradient (% B): 0-5 min 10-95%; Wash. The identity of fusaricidin A was determined by its unique retention time and mass. The relative signal intensities of the fusaricidin peak in the spectra are presented in Table 1 with each intensity normalized to that present in the whole broth spectrum. Fusaricidin A concentrated in the pellet fraction with a small amount remaining in the supernatant fraction.

The colony forming units present in each fraction were also quantified by making serial dilutions of whole broth culture, supernatant fraction, and pellet fraction and plating the dilutions on solid medium. The resulting colonies were counted and recorded (see Table 1). As expected, the majority of the cells moved into the pellet fraction with centrifugation.

TABLE 1

Colony Forming Units (CFU) and relative quantities of fusaricidin A in a whole broth culture of *Paenibacillus* sp. NRRL B-50972.

| Sample | Relative Amount of Fusaricidin A | CFU/g |
| --- | --- | --- |
| Whole Broth | 1.00 | $2.0 \times 10^7$ |
| Supernatant | 0.11 | $1.3 \times 10^5$ |
| Pellet (broth concentrate) | 2.16 | $9.4 \times 10^7$ |
| Whole Broth from an Independent Fermentation | 0.93 | Not measured |

Antifungal activities of the fractions were also measured in an in vivo assay with *Botrytis cinerea* (BOTRCI). The *Paenibacillus* sp. NRRL B-50972 whole broth and corresponding supernatant and pellet fractions were each diluted in water to equivalent final volumes. The diluted whole broth, supernatant fraction, and pellet fraction were applied to young plants which were subsequently exposed to an inoculum of *Botrytis cinerea* (BOTRCI). Several days after exposure to the inoculum of plant pathogen, each plant was scored for percent control of the pathogen relative to the untreated control plants. Each treatment was evaluated with several replicates.

The results shown in FIG. 1 demonstrate that the greatest antifungal activity was present in the whole broth ("WB") and pellet fraction ("Pellets") whereas the supernatant fraction ("Sup") provided little observable antifungal activity compared to the untreated control ("Water").

These experimental data indicate that the antifungal compounds in *Paenibacillus* sp. NRRL B-50972 whole broth can be enriched or concentrated by centrifuging the whole broth and removing the supernatant from the resulting pellet.

Example 2. Identification of a Centrifugation Processing Aid for *Paenibacillus* sp. NRRL B-50972 Whole Broth

Figure 2:
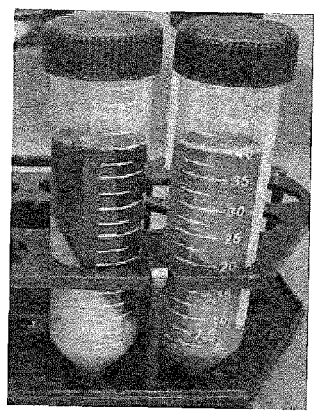
Figure 2:
Figure 2:
Figure 3:
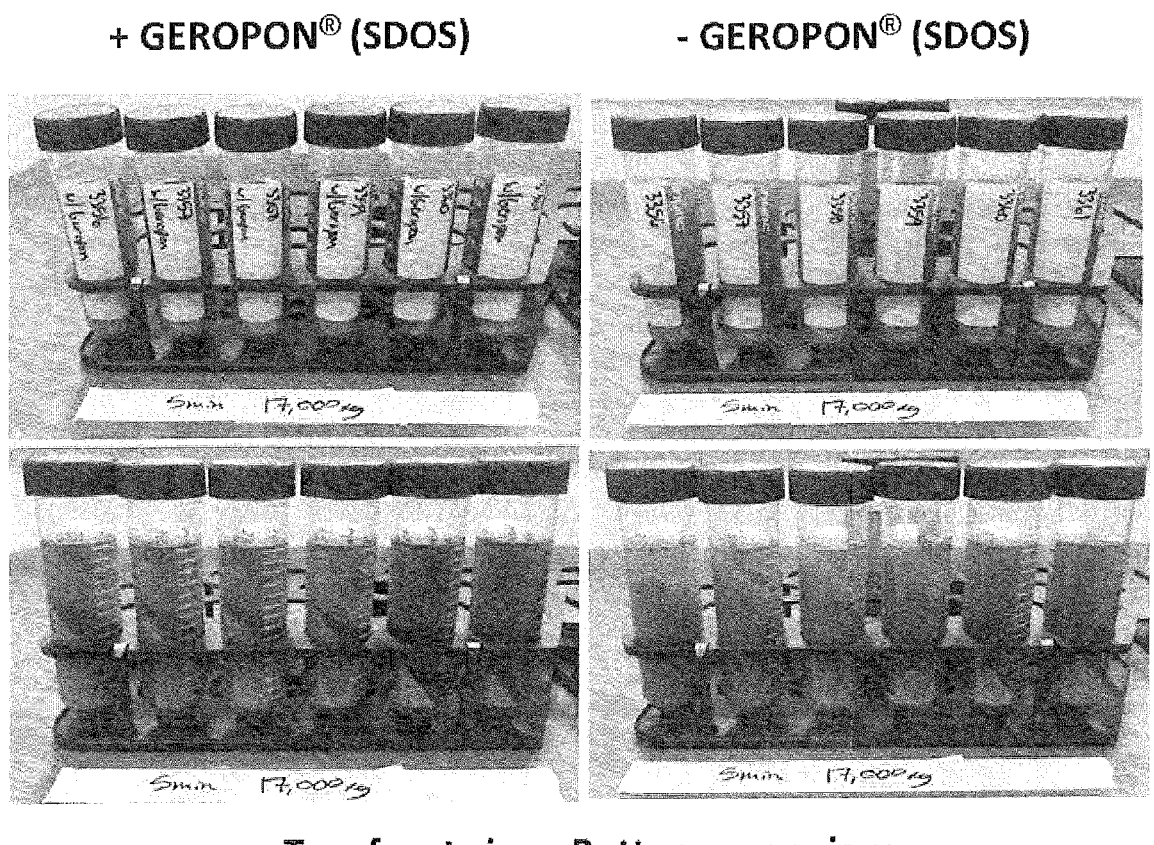
Figure 4:
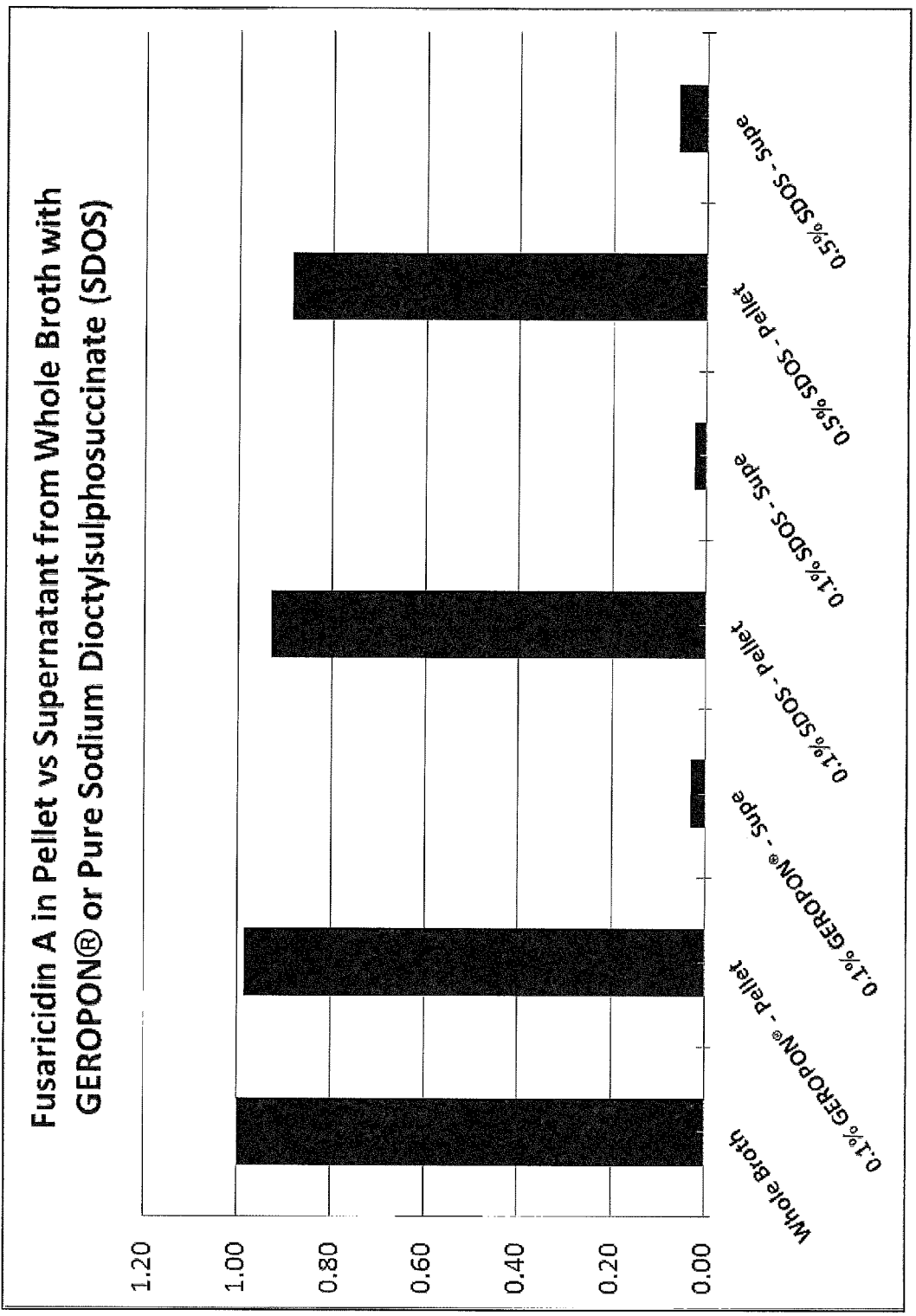
Figure 5A:
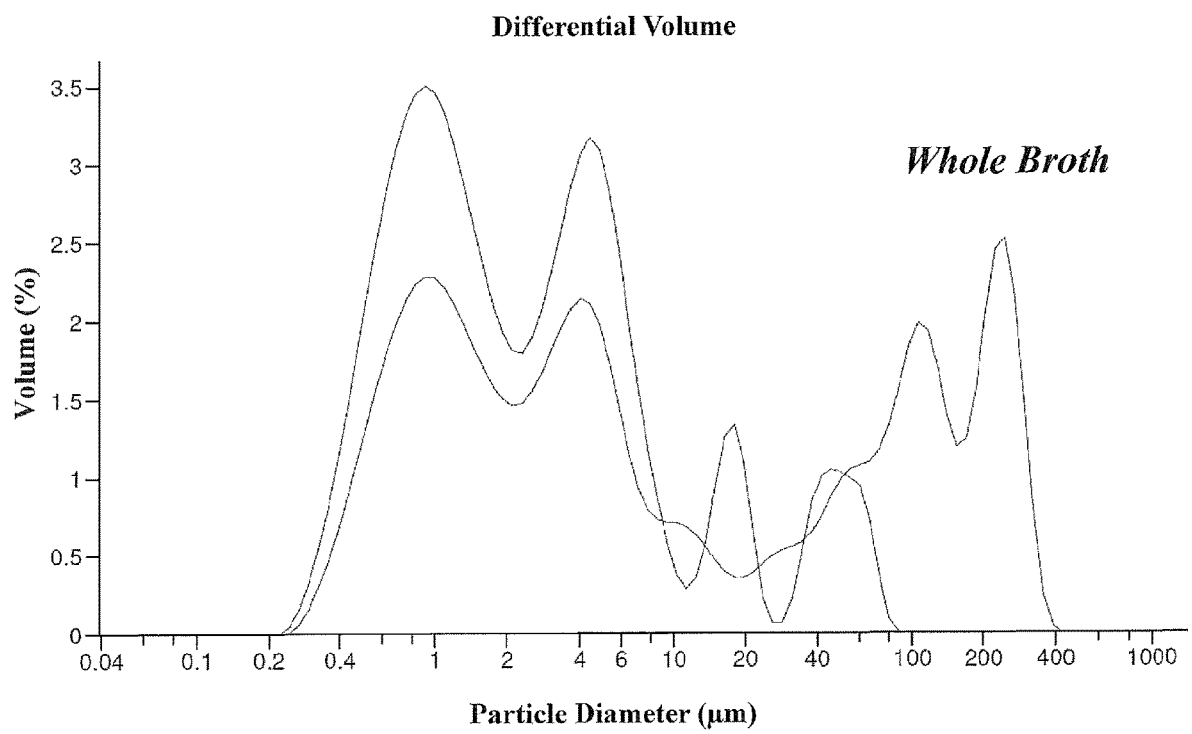
Figure 5B:
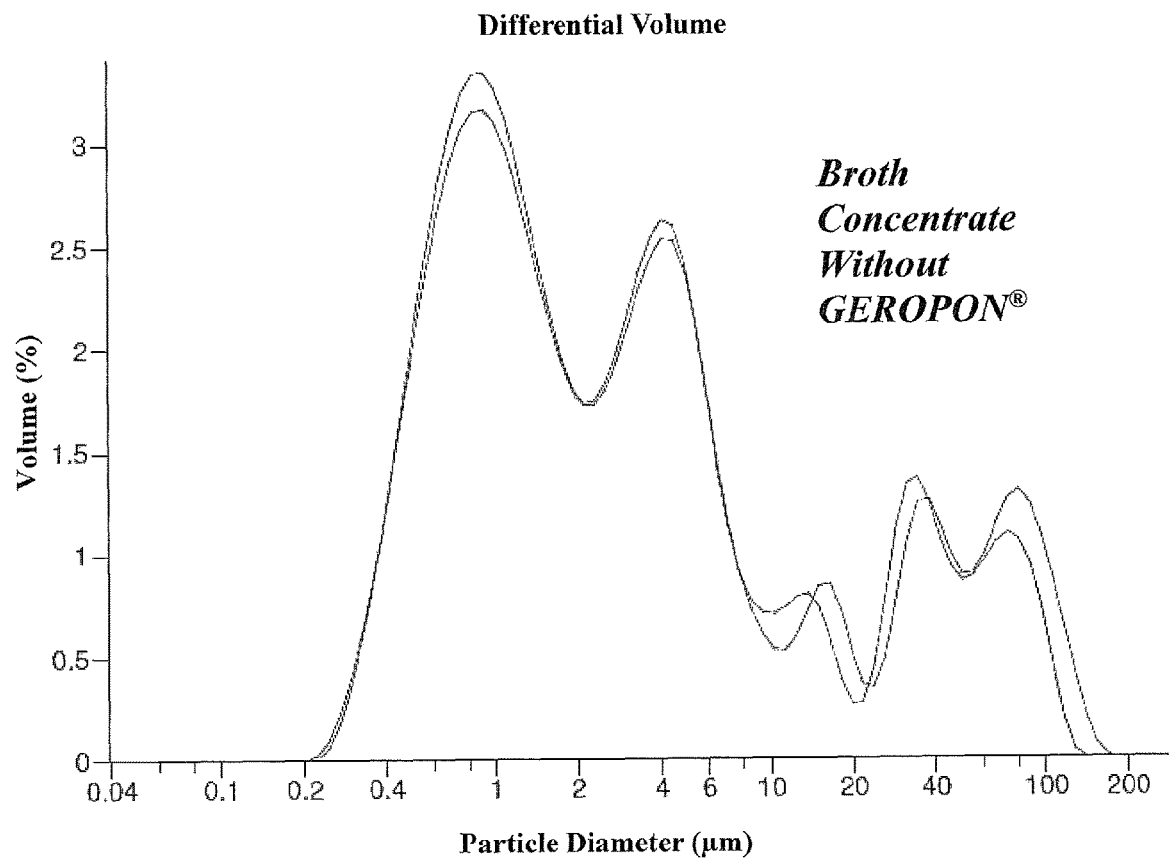
Figure 5C:
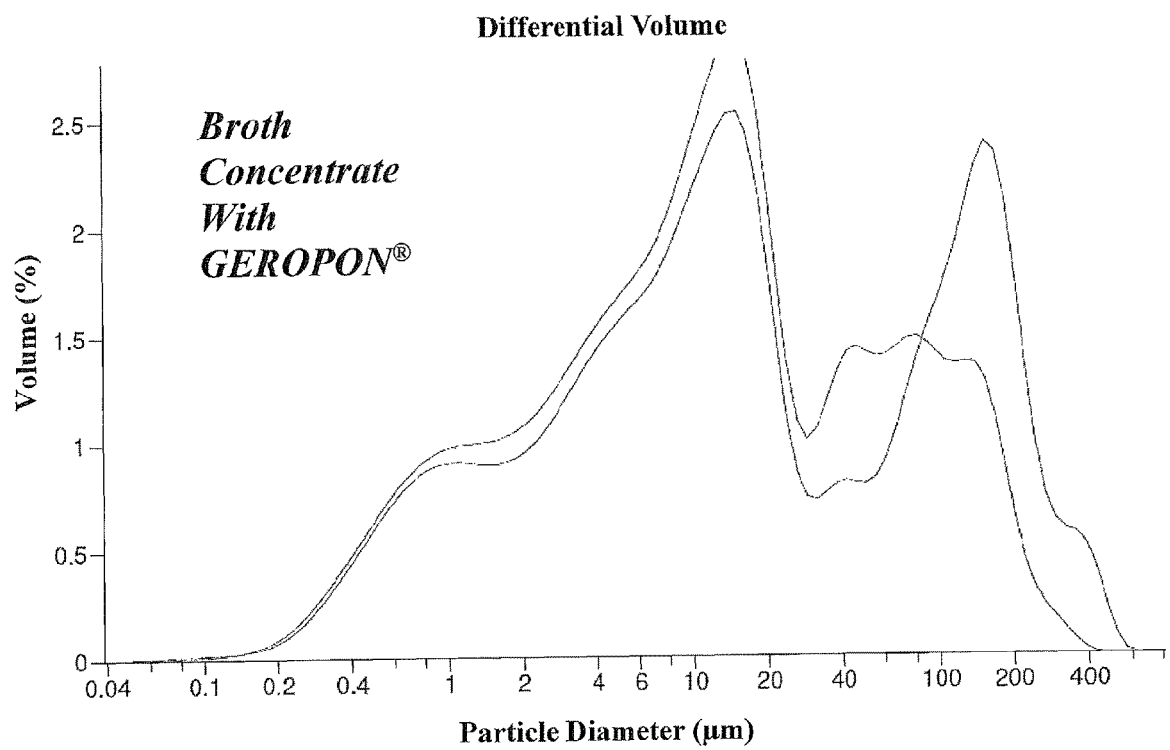
Figure 5D:
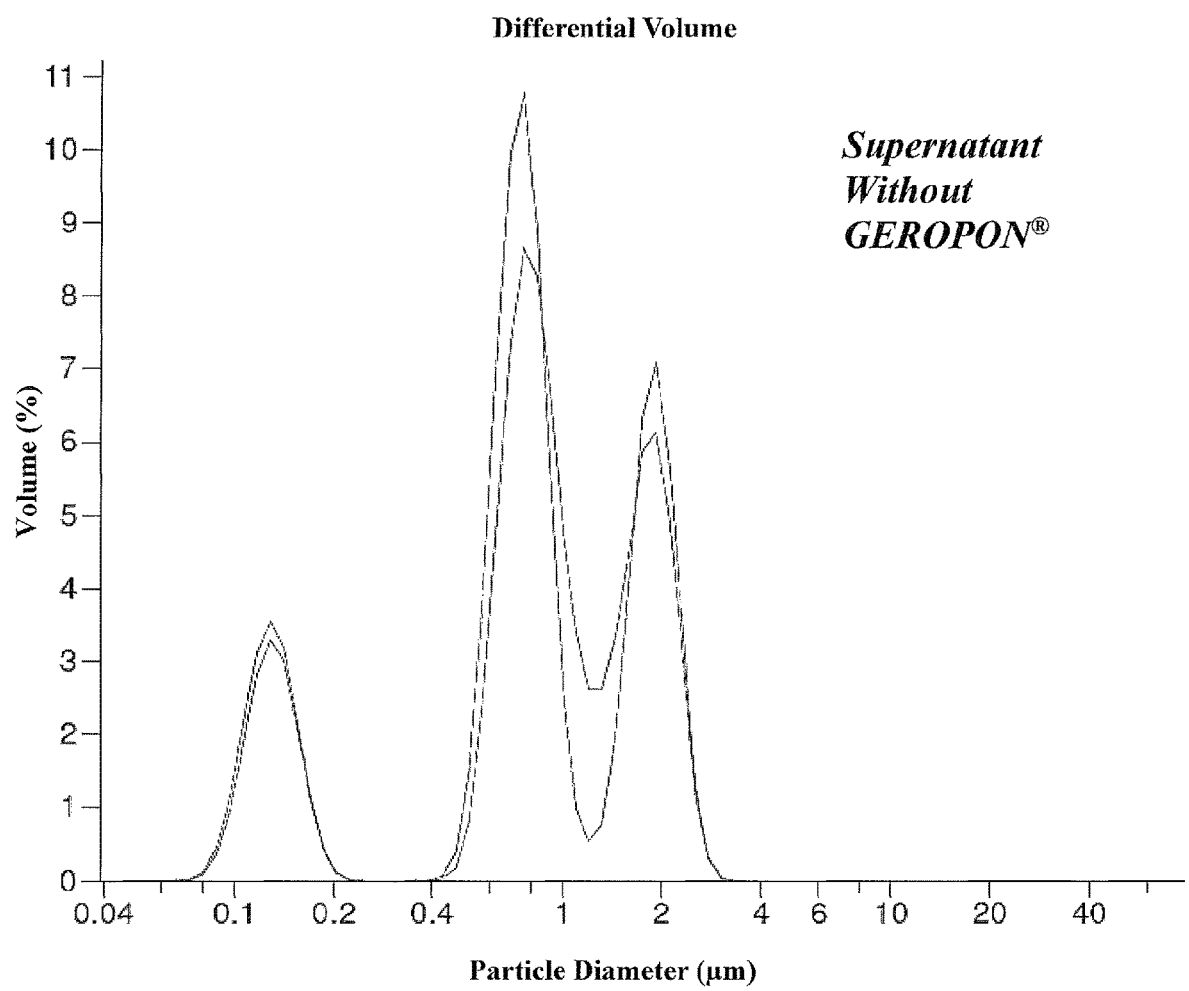
Figure 5E:
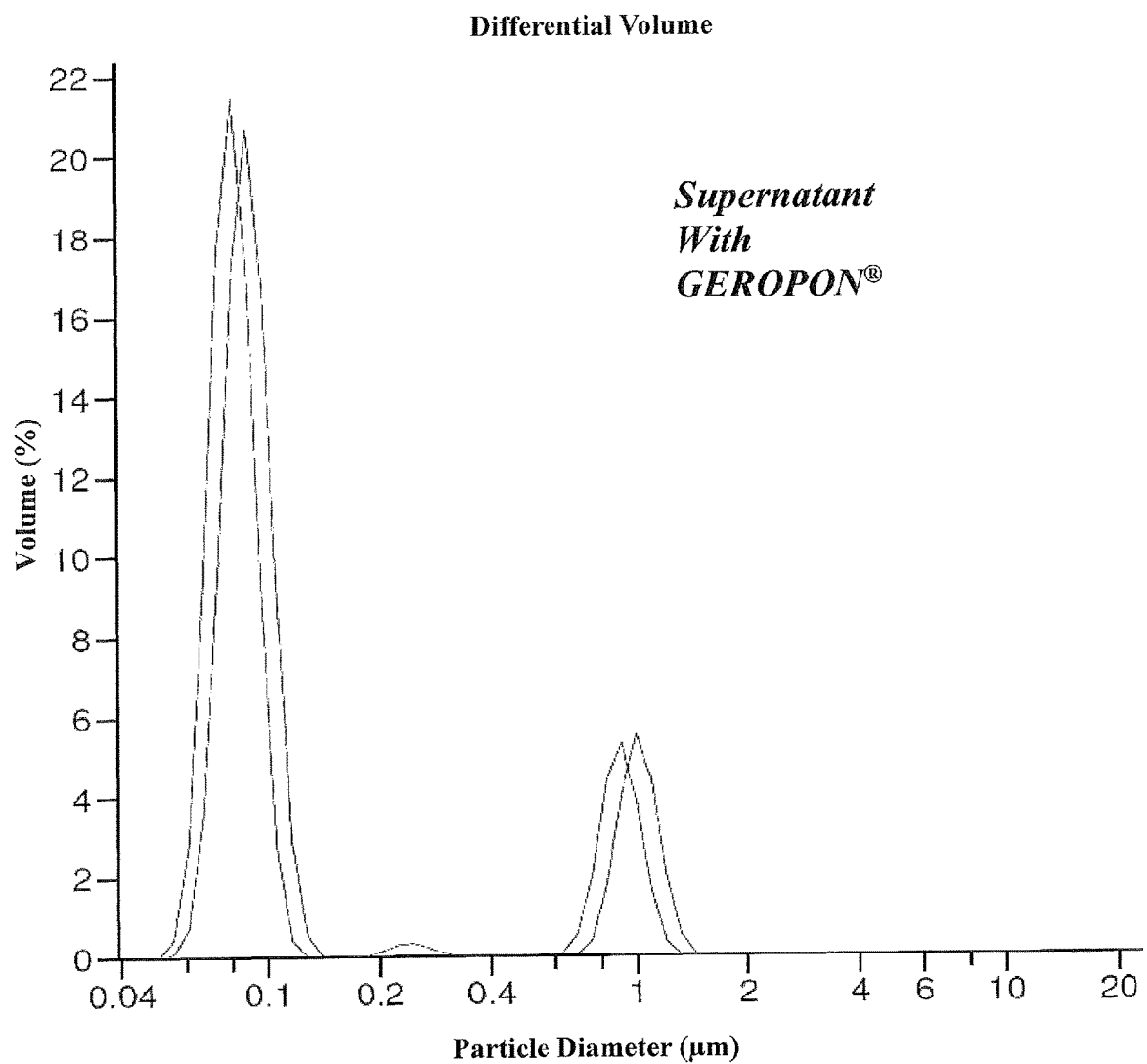

*Paenibacillus* sp. NRRL B-50972 whole broth contains viscous biopolymers such as exopolysaccharides (EPS) that make it difficult to produce a compact pellet fraction by centrifugation. This can be seen in the photographs of pellets from whole broth centrifuged without any processing aid labeled "WB–SDOS" in FIG. 2. After testing various chemical agents for their ability to induce the formation of a compact pellet fraction during centrifugation, GEROPON® (sodium dioctylsulphosuccinate; also known as SDOS) was identified.

When GEROPON® (SDOS) was added to the *Paenibacillus* sp. NRRL B-50972 whole broth ("WB") at a concentration of between 0.1% and 0.5% (w/v) centrifugation of the mixture resulted in a compact pellet fraction and a supernatant relatively free from particulate matter. This can be seen in the photographs of centrifuged whole broth mixed with GEROPON® (SDOS) labeled "WB+SDOS" in FIG. 2.

Example 3. Effect of Centrifugation Processing Aid with Whole Broth from Another *Paenibacillus* Strain To investigate whether GEROPON® (SDOS) could induce the formation of a compact pellet fraction during centrifugation with other EPS-producing strains another *Paenibacillus* strain known to produce relatively high levels of EPS was grown in a soy-based medium. Several preparations of the whole broth were centrifuged at an RCF of 17,000×g for 5 minutes with and without GEROPON® (SDOS) at a concentration of between 0.1% and 0.5% (w/v).

As shown in FIG. 3, addition of GEROPON® (SDOS) to the whole broth from the EPS-producing *Paenibacillus* strain consistently resulted in a compact pellet fraction and a clear supernatant fraction. In contrast, centrifugation of the same whole broth without the GEROPON® (SDOS) generally produced a diffuse pellet fraction and a cloudy supernatant fraction.

Example 4. Confirmation that SDOS Induces Formation of a Compact Pellet Fraction and Measurement of Fusaricidin a in Pellet and Supernatant Fractions GEROPON® (SDOS) is a commercial product available from Solvay (Brussels, Belgium). To confirm that the SDOS in the GEROPON® was responsible for the centrifugation effect and not another chemical component in the commercial product, a purified preparation of SDOS was purchased from Sigma-Aldrich (St. Louis, Mo.). The experiment described in Example 2 was repeated with GEROPON® (SDOS) added to the whole broth to a final concentration of 0.1% or the purified SDOS added to final concentrations of 0.1% or 0.5%. Compact pellet fractions were produced with either the GEROPON® (SDOS) or the purified SDOS.

The analytical method described in Example 1 was then used to determine the relative levels of fusaricidin A in the whole broth and the pellet and supernatant fractions containing GEROPON® (SDOS) or the purified SDOS. Equivalent volumes of the whole broth, pellet fraction, and supernatant fraction were analyzed for fusaricidin A levels which were normalized to the signal produced by fusaricidin A in the whole broth. The majority of the fusaricidin A separated into the pellet fractions with very little remaining in the supernatant fractions (see FIG. 4).

The pellet fractions in these experiments represented between one-fourth and one-third of the original volume, and the supernatant fraction accounted for the remaining volume as observed in Example 1. As the pellet fraction represented a concentrated form of whole broth, one would have expected the relative amounts of fusaricidin A in the pellet fraction to be considerably higher than those detected in the whole broth (see, e.g., the fusaricidin A levels in the whole broth and pellet fraction in Table 1). However, in pellet fractions formed with GEROPON® (SDOS) this was not the case (compare the fusaricidin A levels in whole broth and pellet fractions in FIG. 4). These results suggested that while GEROPON® (SDOS) facilitated the formation of a compact pellet fraction from the whole broth at relatively low centrifugation speeds it also decreased the amount of fusaricidin A detectable with the chromatographic method described in Example 1. This analytical method relies on the ability of the chromatography column to separate fusaricidin A from other compounds and would not detect fusaricidin A bound in large, insoluble aggregates.

Example 5. Analysis of Particle Sizes in
Paenibacillus sp. NRRL B-50972 Culture Broth
with and without GEROPON® (SDOS)

The experimental results suggested that GEROPON® (SDOS) induced the formation of large aggregates of spores, fusaricidin A, and other materials in the Paenibacillus sp. NRRL B-50972 whole broth and these aggregates produced a compact pellet fraction during centrifugation at relatively low speeds. To investigate whether aggregation was occurring with the GEROPON® (SDOS) a particle size analysis (PSA) was performed.

A PSA measures the particle size distribution in a liquid suspension sample. A laser light is passed through a liquid particle suspension. The angular variation in intensity of light scattered is recorded as the laser beam passes through the sample. This angular intensity dependence is then used to generate the particle size distribution. The resulting data curve represents the particle size as a function of the population of particles of that size.

A PSA was performed with Paenibacillus sp. NRRL B-50972 whole broth, a broth concentrate with and without GEROPON® (SDOS), and supernatant fractions from Paenibacillus sp. NRRL B-50972 whole broth with and without GEROPON® (SDOS). The broth concentrate was made up of pellet fractions from the Paenibacillus sp. NRRL B-50972 whole broth after high speed centrifugation without GEROPON® (SDOS) or low speed centrifugation with GEROPON® (SDOS) with a small amount of supernatant that was difficult to remove from the pellet. The resulting data curves are shown in FIGS. 5A-5E. The two curves in each graph represent two measurements taken with each sample.

The PSA data curves for the broth concentrate with GEROPON® (SDOS) identified populations of particles with larger diameters than those observed with the broth concentrate without GEROPON® (SDOS). The majority of the particles from the broth concentrate with GEROPON® (SDOS) exhibited a diameter of 6 µm or greater. In contrast, most of the particles from the broth concentrate without GEROPON® (SDOS) exhibited a diameter of less than 6 µm (compare FIG. 5B and FIG. 5C). These results confirmed the hypothesis that the GEROPON® (SDOS) induced formation of large aggregates.

Analysis of the supernatant fractions with and without GEROPON® (SDOS) further confirmed this hypothesis. The majority of the particles in the supernatant fraction from the whole broth with GEROPON® (SDOS) exhibited diameters of less than 0.4 µm whereas most of the particles in the supernatant fraction from the whole broth without GEROPON® (SDOS) had diameters of greater than 0.4 µm (compare FIG. 5D and FIG. 5E). These data suggest that addition of GEROPON® (SDOS) to the Paenibacillus sp. NRRL B-50972 whole broth induces the formation of large aggregates that are effectively removed from the supernatant fraction and sediment with the pellet fraction during centrifugation.

Example 6. Effect of pH and Salt Concentration on
Pellet Formation and Fusaricidin A Levels Antifungal compounds such as fusaricidin A often carry ionizable groups that are influenced by the pH of the solution in which they are dissolved. The electric charge of these ionizable groups impacts how the antifungal compounds interact with other compounds in the solution. To identify pH's that improve the ability of GEROPON® (SDOS) to induce formation of aggregates in the Paenibacillus sp. NRRL B-50972 whole broth the pH of the whole broth was adjusted between 3 and 10 by adding hydrochloric acid and sodium hydroxide prior to centrifugation.

Figure 6:
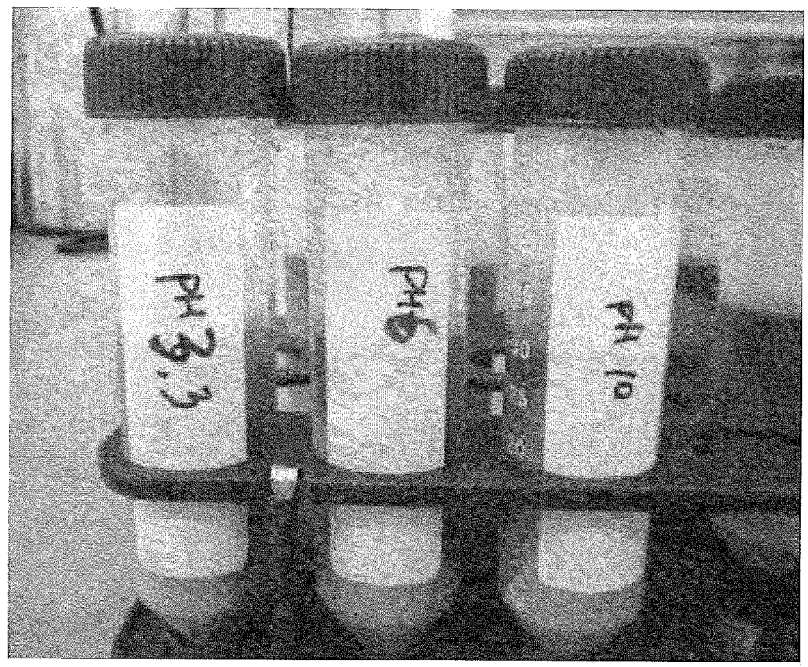
Figure 6:
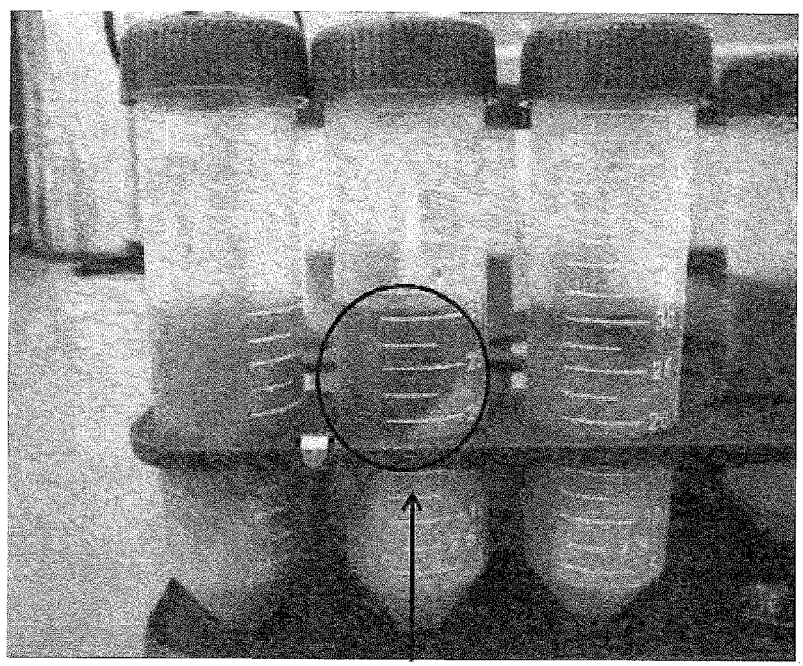

Observation of the pellet fractions after low speed centrifugation with whole broth containing GEROPON® (SDOS) at pH 3, 6, or 10 demonstrated that a compact pellet fraction with a clear supernatant was produced at pH 6 (see FIG. 6). This experiment was repeated with Paenibacillus sp. NRRL B-50972 whole broth containing GEROPON® (SDOS) adjusted to a pH of 3, 4, 5, 6, 7, 8, 9 or 10. After centrifugation, the pellet fractions were separated from the supernatant fractions and the relative fusaricidin A levels in the pellet fractions determined as described in Example 1. The highest fusaricidin A levels were detected in pellet fractions from whole broths with a pH between 4 and 7.

Salt concentration affects the ionic strength of a solution. High salt concentrations can shield dipole interactions and decrease the hydration of polar compounds allowing the "salting-out" of these compounds from the solution. Various concentrations of salt (e.g., sodium chloride or potassium chloride) were added to the Paenibacillus sp. NRRL B-50972 to determine their effect on the formation of a compact pellet fraction after low speed centrifugation with GEROPON® (SDOS). Salt concentrations of between about 2% and about 10% facilitated the formation of a compact pellet fraction.

Example 7. Identification of Additional
Centrifugation Processing Aids with Paenibacillus
sp. NRRL B-50972 Whole Broth After GEROPON® (SDOS) was identified, additional chemical agents were evaluated for their ability to produce a similar effect with Paenibacillus sp. NRRL B-50972 whole broth. Each chemical agent was mixed with whole broth in 50 mL conical vials at a concentration of between 0.1% and 0.5% (w/v) and centrifuged at a relatively low centrifugation speed producing an RCF of 3,000×g for 5 minutes.

Figure 7A:
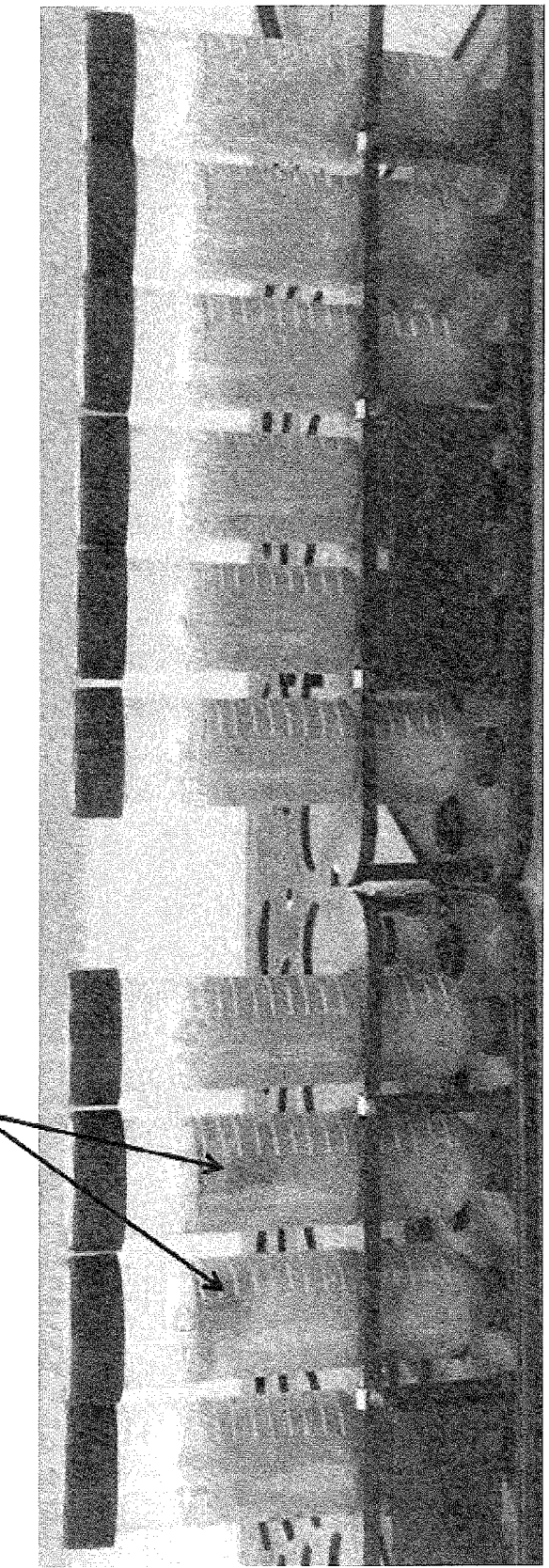

The centrifuged whole broths mixed with the various chemical agents were then compared to the centrifuged whole broth without any chemical agent (i.e., the leftmost conical vial in FIG. 7A). Several chemical agents produced a clear supernatant after low speed centrifugation (i.e., an RCF of 3,000×g) and were investigated further. As demonstrated in Example 1, centrifugation at an RCF of 24,790×g was required to form an identifiable pellet fraction in the absence of these chemical agents.

Figure 7B:
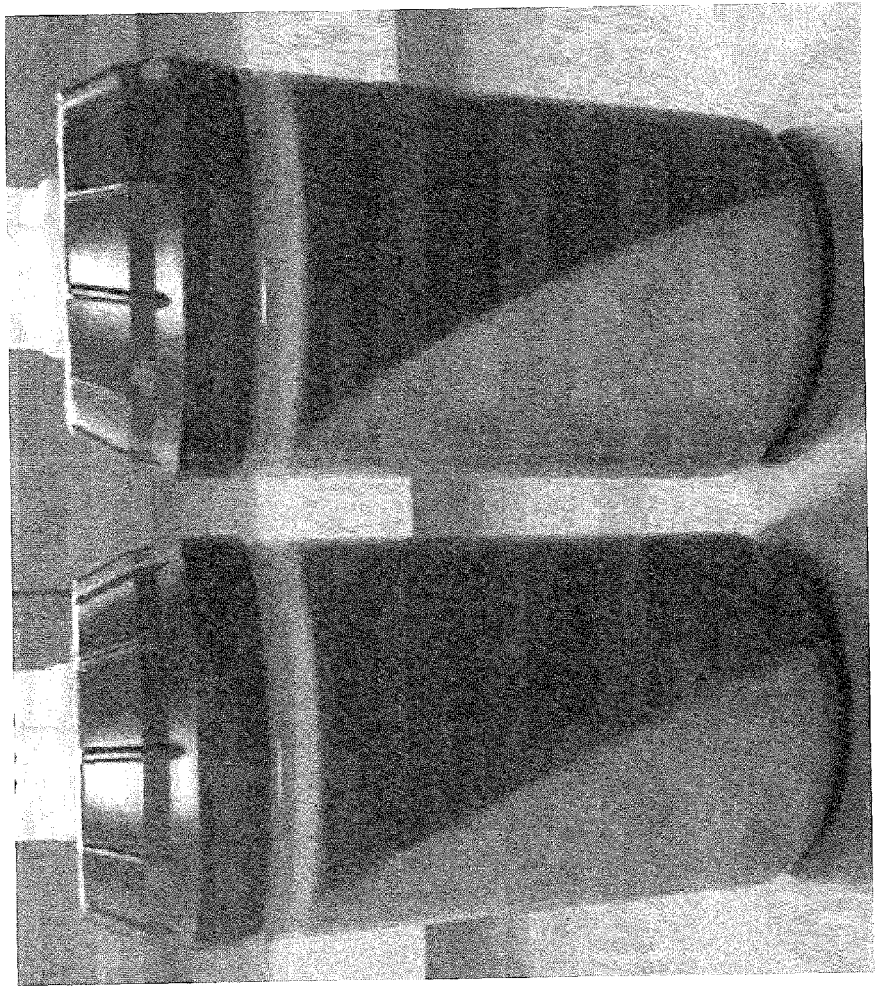
Figure 8:
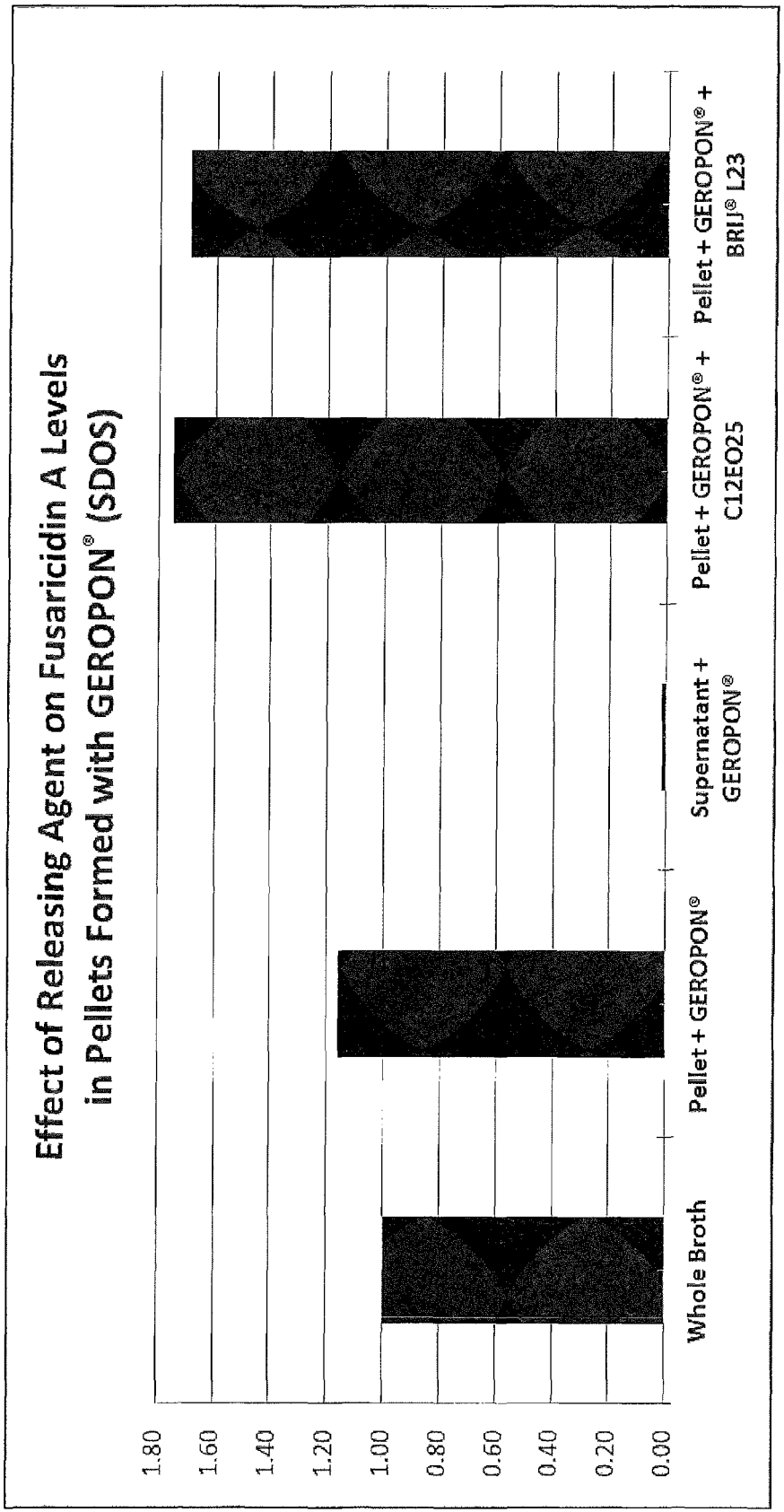
Figure 10:
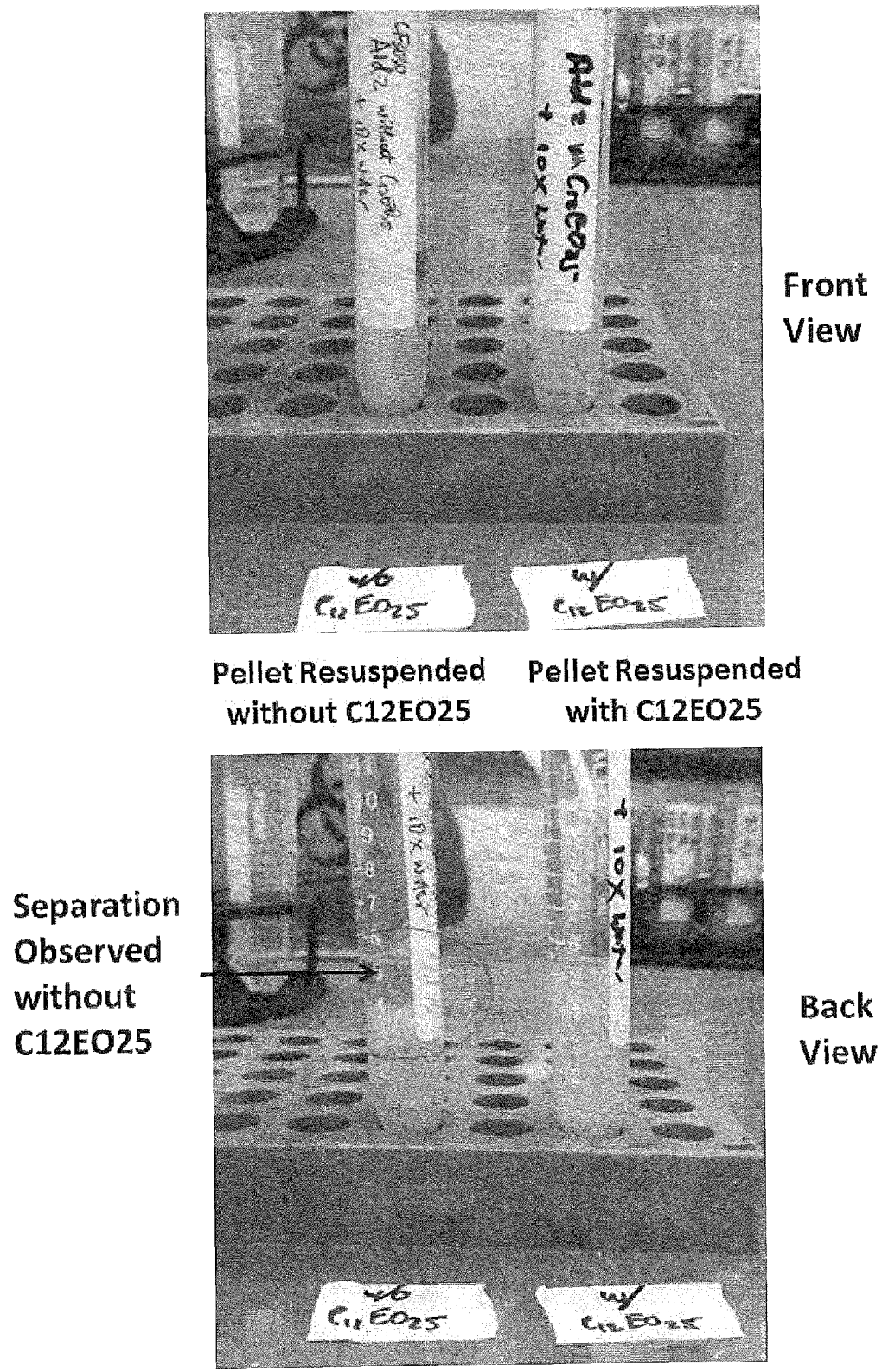

Chemical agents that improved the packing of the pellet fraction from the whole broth were tested with larger volumes to confirm this effect. GEROPON® (SDOS) was included in these confirmation experiments as a positive control. FIG. 7B shows a photograph of the pellet and supernatant fractions from one such experiment confirming that NIAPROOF® 4 (sodium 7-ethyl-2-methyl-4-undecanyl sulfate) produces a similar effect to that observed with GEROPON® (SDOS).

NIAPROOF® 4 (sodium 7-ethyl-2-methyl-4-undecanyl sulfate); NIAPROOF® 8 (sodium 2-ethylhexyl sulfate), and the linear alkylbenzenesulfonate, sodium dodecylbenzesulfonate, enabled formation of a compact pellet fraction after a low speed centrifugation of *Paenibacillus* sp. NRRL B-50972 whole broth.

Example 8. Identification of a Releasing Aid for the Antifungal Compounds in the *Paenibacillus* sp. NRRL B-50972 Pellet Fraction The PSA analysis of broth concentrates and supernatant fractions with and without GEROPON® (SDOS) indicated that addition of a centrifugation aid (e.g., GEROPON® (SDOS)) induced formation of aggregates that more readily formed a compact pellet fraction upon centrifugation (see FIGS. 5A-5E). It followed that a releasing aid added after centrifugation and isolation of the pellet fraction might disrupt the aggregates and increase the bioavailability of the antifungal compounds and the efficacy of the resulting fermentation product.

Several chemical compounds were tested with the pellet fractions for their ability to act as releasing aids. To evaluate the efficacy of the compounds as releasing aids a pellet fraction was generated with GEROPON® (SDOS) from whole broth as described in Example 2. Portions of the pellet fraction were then mixed with the various chemical compounds and the amount of fusaricidin A present in each sample was determined with the analytical method described in Example 1. All measurements of fusaricidin A were normalized to the amount present in the starting material whole broth. The pellet fraction with only GEROPON® (SDOS) was included as a control.

Several polyoxyethylene glycol alkyl ether compounds were found to increase the relative amount of fusaricidin A present in the pellet fraction. These compounds included polyoxyethylene (25) dodecyl ether (also known as C12EO25) and BRIJ® L23 (polyoxyethylene (23) dodecyl ether; also known as C12EO23) (see FIG. 8). Additional experiments demonstrated that the polyoxyethylene glycol alkyl ether compounds C12EO6 (polyoxyethylene (6) dodecyl ether) and BRIJ® S100 (polyoxyethylene (100) octadecyl ether) also increased the relative amount of fusaricidin A present in the pellet fraction (see FIG. 9). TWEEN® 80 (2-[2-[3,4-bis(2-hydroxyethoxy)oxolan-2-yl]-2-(2-hydroxyethoxy)ethoxy]ethyl (E)-octadec-9-enoate; also known as polyoxyethylene sorbitan oleate) was also found to function as a releasing aid (see FIG. 9).

Example 9. Increased Suspensibility of Pellet Fraction after Addition of Releasing Aid The physical properties of the pellet fraction with the GEROPON® (SDOS) alone or with both the GEROPON® (SDOS) and C12EO25 were investigated. One of the physical properties investigated was the suspensibility of the concentrated pellet fraction.

*Paenibacillus* sp. NRRL B-50972 was cultured in a soy-based medium and subjected to low-speed centrifugation with GEROPON® (SDOS) to produce a pellet fraction. The pellet fraction was separated into two fractions and C12EO25 was mixed with one of the fractions. Aliquots from both fractions were mixed with water in 15 mL conical vials to make 10-fold dilutions. The diluted pellet fractions were allowed to equilibrate at room temperature for several minutes.

After equilibration, the pellet fraction without C12EO25 separated into two layers with a transparent layer on top and a cloudy layer on the bottom (see the conical vial on the left in FIG. 10). In contrast, the pellet fraction containing C12EO25 remained as a single suspension after equilibration (see the conical vial on the right in FIG. 8). These results demonstrated that C12EO25 increases the suspensibility of the *Paenibacillus* sp. NRRL B-50972 broth concentrate when diluted in water.

Example 10. Increased Antifungal Activity of *Paenibacillus* sp. NRRL B-50972 Whole Broth with Addition of Centrifuge Aid and Releasing Aid

*Paenibacillus* sp. NRRL B-50972 was cultured in a soy-based medium to produce a whole broth. 0.1% GEROPON® (SDOS) and 2% KCl were added to a portion of the whole broth and the pH adjusted to 6. This portion of the whole broth was centrifuged to generate a pellet fraction (i.e., a broth concentrate), and the supernatant fraction was removed. A portion of the pellet fraction was then mixed with the releasing aid, C12EO25.

The whole broth, pellet fraction with only GEROPON® (SDOS), and pellet fraction with both GEROPON® (SDOS) and C12EO25 were diluted in water to concentrations of 10%, 5%, 2.5%, and 1.25%. The diluted whole broths were applied to young plants which were subsequently exposed to an inoculum of *Alternaria solani* (ALTESO) or *Botrytis cinerea* (BOTRCI). Several days after exposure to the inoculum of plant pathogen, each plant was scored for percent control of the pathogen relative to the untreated control (UTC) plants. Each treatment was evaluated with three replicates and the average percent control reported (see Tables 2-3).

In each of the assays, the pellet fraction with only GEROPON® (SDOS) had greater antifungal activity than the whole broth, and the pellet fraction with both GEROPON® (SDOS) and C12EO25 had the greatest antifungal activity. These experimental data indicate that addition of GEROPON® (SDOS) to the *Paenibacillus* sp. NRRL B-50972 whole broth allows enrichment or concentration of the antifungal compounds in a pellet fraction during a low speed centrifugation and addition of C12EO25 enhances the antifungal activity of this pellet fraction.

GEROPON® (SDOS) and C12EO25 were also each applied to young plants at final rates similar to those in the pellet fractions. The young plants were later inoculated with fungal pathogen and the each plant was scored for percent control of the pathogen relative to the UTC plants. These control treatments demonstrated that GEROPON® (SDOS) and C12EO25 had no inherent antifungal activity that could be identified after comparison with the UTC plants.

TABLE 2

Control of *Alternaria solani* (ALTESO) achieved with a *Paenibacillus* sp. NRRL B-50972 Whole Broth, a resuspended Pellet Fraction with GEROPON ® (SDOS), and a resuspended Pellet Fraction with GEROPON ® (SDOS) and C12EO25 at dilution rates of 10%, 5%, 2.5%, and 1.25%.

| Treatment | Application Rate | Average Percent Control |
|---|---|---|
| Whole Broth | 10% | 98 |
| | 5% | 78 |
| | 2.5% | 78 |
| | 1.25% | 57 |

TABLE 2-continued

Control of *Alternaria solani* (ALTESO) achieved with
a *Paenibacillus* sp. NRRL B-50972 Whole Broth, a resuspended
Pellet Fraction with GEROPON ® (SDOS), and a
resuspended Pellet Fraction with GEROPON ® (SDOS)
and C12EO25 at dilution rates of 10%, 5%, 2.5%, and 1.25%.

| Treatment | Application Rate | Average Percent Control |
|---|---|---|
| Pellet Fraction + GEROPON ® (SDOS) | 10% | 98 |
| | 5% | 96 |
| | 2.5% | 80 |
| | 1.25% | 82 |
| Pellet Fraction + GEROPON ® (SDOS) + C12EO25 | 10% | 99 |
| | 5% | 96 |
| | 2.5% | 94 |
| | 1.25% | 93 |

TABLE 3

Control of *Botrytis cinerea* (BOTRCI) achieved with
a *Paenibacillus* sp. NRRL B-50972 Whole Broth, a resuspended
Pellet Fraction with GEROPON ® (SDOS), and a
resuspended Pellet Fraction with GEROPON ® (SDOS)
and C12EO25 at dilution rates of 10%, 5%, 2.5%, and 1.25%.

| Treatment | Application Rate | Average Percent Control |
|---|---|---|
| Whole Broth | 10% | 63 |
| | 5% | 75 |
| | 2.5% | 68 |
| | 1.25% | 28 |
| Pellet Fraction + GEROPON ® (SDOS) | 10% | 89 |
| | 5% | 93 |
| | 2.5% | 60 |
| | 1.25% | 73 |
| Pellet Fraction + GEROPON ® (SDOS) + C12EO25 | 10% | 100 |
| | 5% | 98 |
| | 2.5% | 94 |
| | 1.25% | 75 |

Example 11. Fusaricidin a Levels in Large Scale Preparations of *Paenibacillus* sp. NRRL B-50972 Broth Concentrates with Centrifuge Aid and Releasing Aid Five separate large batches of broth concentrate from *Paenibacillus* sp. NRRL B-50972 whole broth were prepared as described in Example 10 using GEROPON® (SDOS) as a centrifuge aid and BRIJ® S100 (polyoxyethylene (100) octadecyl ether) as a releasing aid. Each batch constituted several liters of material. The fusaricidin levels in the whole broth and resulting broth concentrate from each batch were quantified as described in Example 1. All results were normalized to the fusaricidin A levels in a *Paenibacillus* sp. NRRL B-50972 whole broth stored at −80 degrees Celsius (i.e., the "WB Standard").

Figure 11:
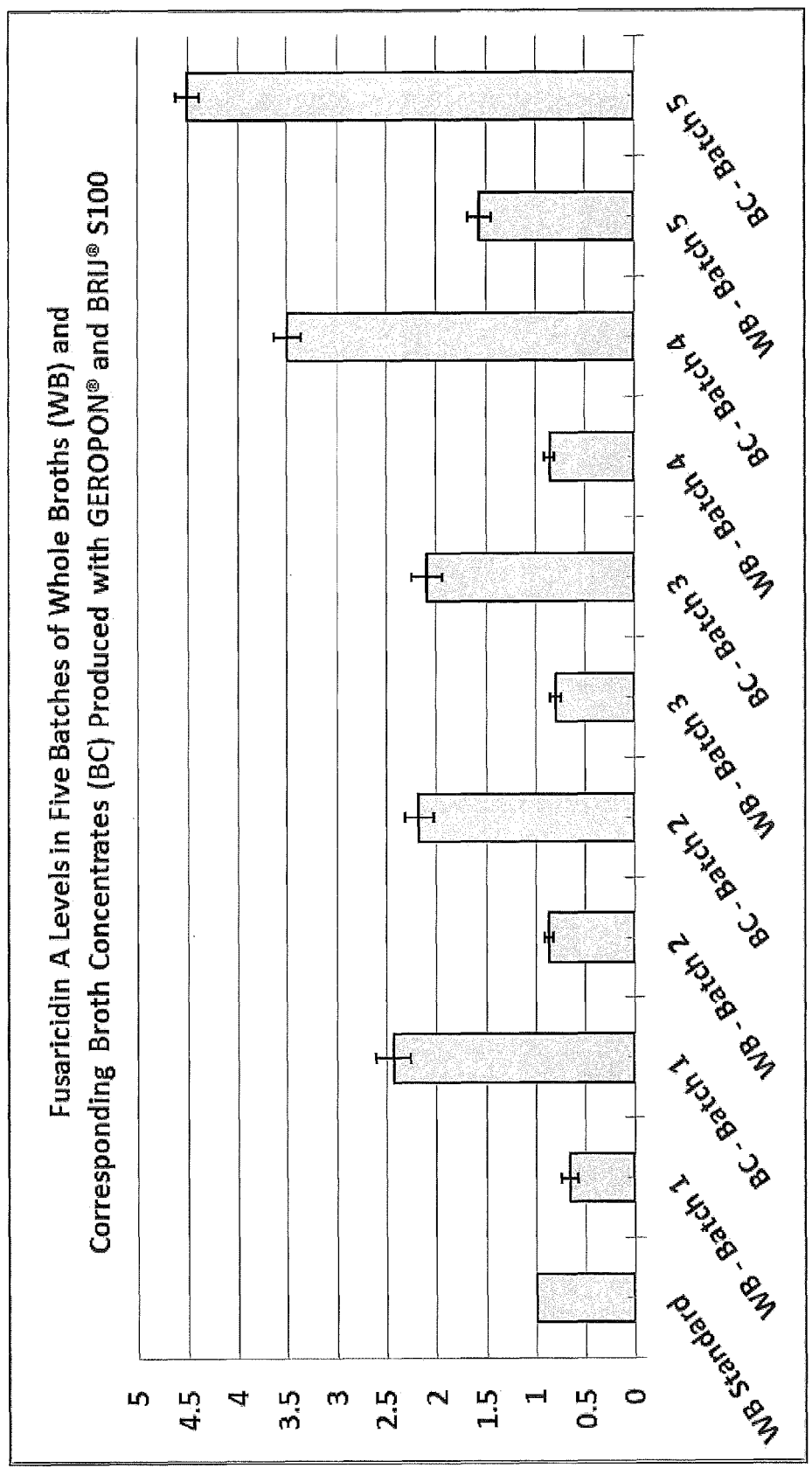

FIG. 11 presents the results with the error bars on the graph indicating the 95% confidence interval in the fusaricidin A measurements. Fusaricidin A levels in the broth concentrates were as much as 3.5 times greater than those detected in the corresponding whole broths.

Example 12. Effect of Centrifugation Processing Aid with *Bacillus subtilis* NRRL B-21661 Whole Broth

*Bacillus subtilis* strain NRRL B-21661 was grown in a soy-based medium. The resulting viscous whole broth was centrifuged at an RCF of 1,500×g for 5 minutes with and without GEROPON® (SDOS) at a concentration of between 0.1% and 0.5% (w/v).

Figure 12:
Figure 12:
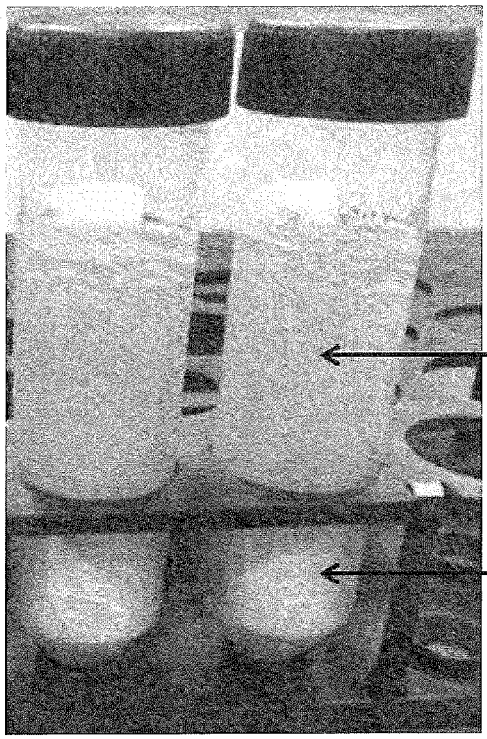

Addition of GEROPON® (SDOS) to the *Bacillus subtilis* strain NRRL B-21661 whole broth resulted in a more compact pellet fraction and a clearer supernatant fraction (see FIG. 12). In contrast, centrifugation of the same whole broth without the GEROPON® (SDOS) produced a relatively diffuse pellet fraction and cloudy supernatant fraction.

Example 13. Confirmation of Increased Antifungal Activity and Dose Response of *Paenibacillus* sp. NRRL B-50972 Whole Broth with Centrifuge Aid and Releasing Aid

*Paenibacillus* sp. NRRL B-50972 whole broth was prepared and processed as described in Example 10. The resulting whole broth, pellet fraction with only GEROPON® (SDOS), and pellet fraction with both GEROPON® (SDOS) and C12EO25 were serially diluted to prepare samples having 1×, 0.5×, 0.25×, and 0.125× the concentration of the starting materials. The serially diluted samples were then applied to young plants at a rate of 0.625%. The plants were inoculated with the fungal pathogen *Alternaria solani* and subsequently evaluated for disease control relative to UTC plants. The reported disease control values are the averages of three independent replicates.

As shown in Table 4, the pellet fraction with only GEROPON® (SDOS) had greater antifungal activity than the whole broth, and the pellet fraction with both GEROPON® (SDOS) and C12EO25 had the greatest antifungal activity. In addition, a clear dose response was observed across each of the samples with the highest activity observed with the 1× samples and the least activity observed with the 0.125× samples.

TABLE 4

Control of *Alternaria solani* (ALTESO) achieved with a
*Paenibacillus* sp. NRRL B-50972 Whole Broth, a resuspended
Pellet Fraction with GEROPON ® (SDOS), and a resuspended
Pellet Fraction with GEROPON ® (SDOS) and C12EO25
at 1X, 0.5X, 0.25X, and 0.125X serial dilutions of each sample.
All sample preparations were applied to plants at a rate of 0.625%.

| Treatment | Serial Dilution | Average Percent Control |
|---|---|---|
| Whole Broth | 1X | 61 |
| | 0.5X | 26 |
| | 0.25X | 16 |
| | 0.125X | 0 |
| Pellet Fraction + GEROPON ® (SDOS) | 1X | 93 |
| | 0.5X | 81 |
| | 0.25X | 39 |
| | 0.125X | 7 |
| Pellet Fraction + GEROPON ® (SDOS) + C12EO25 | 1X | 97 |
| | 0.5X | 88 |
| | 0.25X | 70 |
| | 0.125X | 32 |

Example 14. Fusaricidin A Levels in Whole Broth, Broth Concentrates and Supernatants from Three Different *Paenibacillus* Strains Broth concentrates from *Paenibacillus* sp. NRRL B-50972 whole broth and from whole broths from two additional *Paenibacillus* strains were prepared as described in Example 10 using GEROPON® (SDOS) as a centrifuge aid and BRIJ® S100 (polyoxyethylene (100) octadecyl ether) as a releasing aid. Samples of each whole broth and of the supernatants removed during the production of the broth concentrates were saved for analysis. The fusaricidin levels in the whole broth and resulting broth concentrates and supernatants from each strain were quantified as described in Example 1. All results were normalized to the fusaricidin A levels in a *Paenibacillus* sp. NRRL B-50972 whole broth stored at −80 degrees Celsius.

Figure 13:
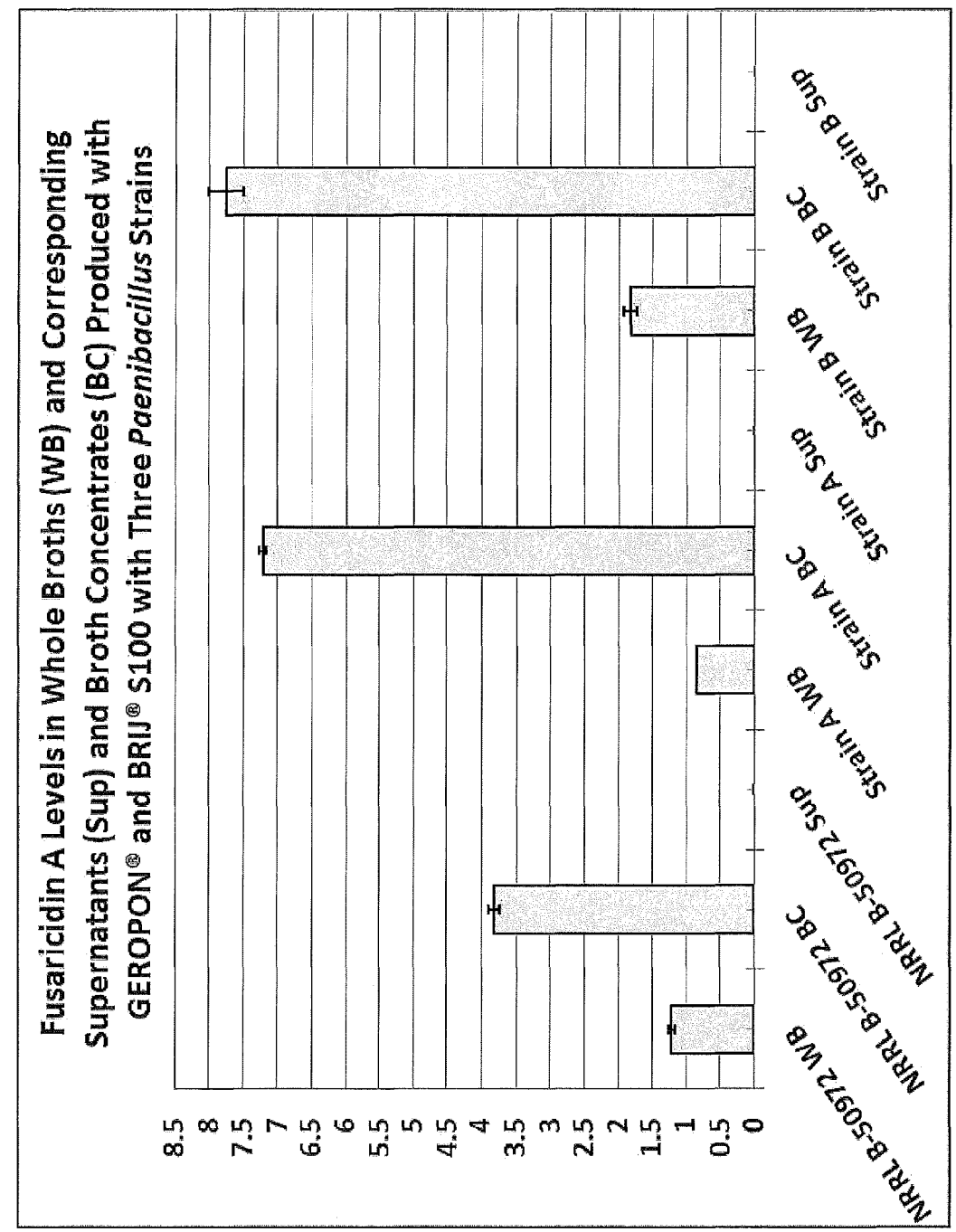

FIG. 13 presents the results with the error bars on the graph indicating the 95% confidence interval in the fusaricidin A measurements. The effective concentration of fusaricidin A going from whole broth to broth concentrate was observed across all three strains with levels in broth concentrates increasing as much as 7 times over those detected in the corresponding whole broths. No detectable fusaricidin A was found in any of the supernatants.

The whole broths, broth concentrates, and supernatants were analyzed for antifungal activity against *Alternaria solani* as described in Example 10. Treatments with BRAVO® (chlorothalonil) were included as positive controls. The results presented in Table 5 demonstrate that antifungal activity was found in the whole broths and broth concentrates with little or no detectable antifungal activity observed in the supernatants.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

TABLE 5

Control of *Alternaria solani* (ALTESO) achieved with whole broths, broth concentrates, and supernatants from *Paenibacillus* sp. NRRL B-50972, *Paenibacillus* sp. Strain A, and *Paenibacillus* sp. Strain B at dilution rates of 5%, 2.5%, and 1.25%.

| Treatment | Application Rate | Average Percent Control |
|---|---|---|
| *Paenibacillus* sp. NRRL B-50972 Whole Broth | 5% | 73 |
|  | 2.50% | 73 |
|  | 1.25% | 81 |
| *Paenibacillus* sp. NRRL B-50972 Broth Concentrate | 5% | 93 |
|  | 2.50% | 93 |
|  | 1.25% | 92 |

TABLE 5-continued

Control of *Alternaria solani* (ALTESO) achieved with whole broths, broth concentrates, and supernatants from *Paenibacillus* sp. NRRL B-50972, *Paenibacillus* sp. Strain A, and *Paenibacillus* sp. Strain B at dilution rates of 5%, 2.5%, and 1.25%.

| Treatment | Application Rate | Average Percent Control |
|---|---|---|
| *Paenibacillus* sp. NRRL B-50972 Supernatant | 5% | 54 |
|  | 2.50% | 31 |
|  | 1.25% | 0 |
| *Paenibacillus* sp. Strain A Whole Broth | 5% | 92 |
|  | 2.50% | 92 |
|  | 1.25% | 90 |
| *Paenibacillus* sp. Strain A Broth Concentrate | 5% | 95 |
|  | 2.50% | 95 |
|  | 1.25% | 95 |
| *Paenibacillus* sp. Strain A Supernatant | 5% | 0 |
|  | 2.50% | 0 |
|  | 1.25% | 0 |
| *Paenibacillus* sp. Strain B Whole Broth | 5% | 93 |
|  | 2.50% | 94 |
|  | 1.25% | 90 |
| *Paenibacillus* sp. Strain B Broth Concentrate | 5% | 95 |
|  | 2.50% | 96 |
|  | 1.25% | 95 |
| *Paenibacillus* sp. Strain B Supernatant | 5% | 0 |
|  | 2.50% | 0 |
|  | 1.25% | 0 |
| BRAVO ® (Chlorothalonil) | 128 ppm | 98 |
| BRAVO ® (Chlorothalonil) | 32 ppm | 92 |

We claim:

1. A method of enriching a lipopeptide in a microbial cell culture, the method comprising:
   a) mixing an amphiphilic sulfonate and/or an amphiphilic sulfate with the cell culture to induce the formation of aggregates containing the lipopeptide;
   b) centrifuging the cell culture to generate a supernatant fraction and a pellet fraction;
   c) separating the pellet fraction from the supernatant fraction; and
   d) mixing the pellet fraction with a polyoxyethylene glycol alkyl ether to release the lipopeptide from the aggregates.

2. The method of claim 1, wherein the lipopeptide is a fusaricidin-type compound selected from the group consisting of fusaricidin A, fusaricidin B, fusaricidin C, fusaricidin D, LI-F03, LI-F04, LI-F05, LI-F06, LI-F07, LI-F08, Paeniserine A1, Paeniserine A2, Paeniserine A3, Paeniserine A4, Paeniserine B1, Paeniserine B2, Paeniserine B3, Paeniserine B4, Paeniserine C1, Paeniserine C2, Paeniserine C3, Paeniserine C4, Paeniprolixin A1, Paeniprolixin A2, Paeniprolixin B1, Paeniprolixin B2, Paeniprolixin C1, Paeniprolixin C2, Paeniprolixin D1, Paeniprolixin D2, Paeniprolixin E1, Paeniprolixin E2, Paeniprolixin F1, Paeniprolixin F2, and combinations thereof.

3. The method of claim 1, wherein an amphiphilic sulfonate is mixed with the cell culture and the amphiphilic sulfonate is a compound of formula (I):

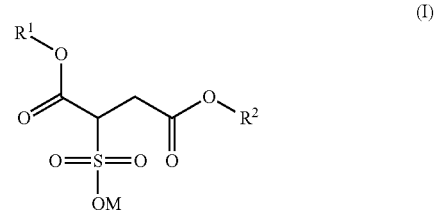

wherein
R¹ and R² are independently a linear or branched $C_{1-20}$ alkyl or a linear or branched $C_{2-20}$ alkene; and
M is $H^+$, $Li^+$, $Na^+$, $K^+$ or $(C_{1-8}\ alkyl)_4N^+$.

4. The method of claim 3, wherein the sulfonate is dioctyl sulfosuccinate; 1,4-bis(2-ethylhexoxy)-1,4-dioxobutane-2-sulfonate; or a $H^+$, $Li^+$, $Na^+$, $K^+$ or $(C_{1-8}\ alkyl)_4N^+$ salt thereof.

5. The method of claim 1, wherein an amphiphilic sulfate is mixed with the cell culture and the amphiphilic sulfate is an alkyl sulfate of formula (II):

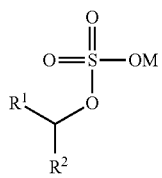

(II)

wherein
R¹ and R² are independently H, a linear or branched $C_{1-20}$ alkyl, or a linear or branched $C_{2-20}$ alkene; and
M is $H^+$, $Li^+$, $Na^+$, $K^+$ or $(C_{1-8}\ alkyl)_4N^+$;
with the proviso that R¹ and R² are not both H.

6. The method of claim 5, wherein the alkyl sulfate is 7-ethyl-2-methyl-4-undecanyl sulfate, 2-ethylhexyl sulfate, or a $Li^+$, $Na^+$, $K^+$ or $(C_{1-8}\ alkyl)_4N^+$ salt thereof.

7. The method of claim 1, wherein an amphiphilic sulfonate is mixed with the cell culture and the amphiphilic sulfonate is a linear alkylbenzenesulfonate or a branched alkylbenzenesulfonate.

8. The method of claim 7, wherein the amphiphilic sulfonate is a linear alkylbenzenesulfonate of formula (III):

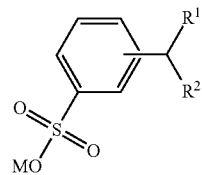

(III)

wherein
R¹ and R² are independently H, a linear or branched $C_{1-20}$ alkyl; and
M is $H^+$, $Li^+$, $Na^+$, $K^+$ or $(C_{1-8}\ alkyl)_4N^+$;
with the proviso that R¹ and R² are not both H.

9. The method of claim 8, wherein the linear alkylbenzenesulfonate is dodecylbenzesulfonate or a $Li^+$, $Na^+$, $K^+$ or $(C_{1-8}\ alkyl)_4N^+$ salt thereof.

10. The method of claim 1, wherein the polyoxyethylene glycol alkyl ether is a compound with a molecular formula of $C_nH_{2n+1}(OCH_2CH_2)_mOH$,
wherein
m is an integer between 1 and 120; and
n is an integer between 1 and 20.

11. The method of claim 10, wherein n is 12 or 18 and/or m is 25 or 100.

12. The method of claim 1, wherein the microbial cell culture comprises a strain of *Paenibacillus* sp., *Bacillus* sp., and/or *Pseudomonas* sp.

13. The method of claim 12, wherein the microbial cell culture comprises *Paenibacillus* sp. strain NRRL B-50972, *Bacillus subtilis* strain NRRL B-21661, and/or a fungicidal mutant strain thereof having all the identifying characteristics of the respective strain.

* * * * *